United States Patent
Freeman et al.

(10) Patent No.: US 11,590,354 B2
(45) Date of Patent: Feb. 28, 2023

(54) WEARABLE MEDICAL DEVICE RESPONSE MECHANISMS AND METHODS OF USE

(71) Applicant: ZOLL Medical Corporation, Chelmsford, MA (US)

(72) Inventors: Gary A Freeman, Waltham, MA (US); Shane S Volpe, Saltsburg, PA (US); James A Patterson, III, Claridge, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 119 days.

(21) Appl. No.: 16/726,283

(22) Filed: Dec. 24, 2019

(65) Prior Publication Data
US 2020/0206518 A1    Jul. 2, 2020

Related U.S. Application Data

(60) Provisional application No. 62/785,805, filed on Dec. 28, 2018.

(51) Int. Cl.
| | |
|---|---|
| *A61N 1/04* | (2006.01) |
| *A61N 1/39* | (2006.01) |
| *A61N 1/362* | (2006.01) |

(52) U.S. Cl.
CPC ........... *A61N 1/3904* (2017.08); *A61N 1/046* (2013.01); *A61N 1/0484* (2013.01); (Continued)

(58) Field of Classification Search
CPC .............. A61N 1/39046; A61N 1/0484; A61N 1/0492; A61N 1/3625; A61N 1/3993
See application file for complete search history.

(56) References Cited

U.S. PATENT DOCUMENTS

| | | |
|---|---|---|
| 4,094,310 A | 6/1978 | McEachern et al. |
| 4,432,368 A | 2/1984 | Russek |

(Continued)

FOREIGN PATENT DOCUMENTS

| | | |
|---|---|---|
| CN | 101031334 | 9/2007 |
| CN | 101657229 | 2/2010 |

(Continued)

OTHER PUBLICATIONS

PCT Search Report and Written Opinion for PCT Application No. PCT/US2019/068472, dated Mar. 26, 2020, 11 pages.

(Continued)

*Primary Examiner* — Eric D. Bertram
(74) *Attorney, Agent, or Firm* — ZOLL Medical Corporation

(57) ABSTRACT

System and methods for providing a patient with arrhythmia treatment are described. For example, a system includes an arrhythmia monitoring and treatment assembly configured to be worn on the torso of the patient. The assembly has a housing discreetly extending from a skin surface of the patient. The assembly is configured to provide therapy on detecting one or more arrhythmia conditions of the patient. A first at least one user response button is disposed on the assembly at a first location on the torso concealed under clothing, and a second at least one user response button is configured to be worn on a second location of the patient's body, a location other than the torso that is accessible to the patient. The system suspends an impending therapy upon receiving a user input from either one of the first or second at least one user response buttons.

23 Claims, 15 Drawing Sheets

(52) U.S. Cl.
CPC ......... *A61N 1/0492* (2013.01); *A61N 1/3625* (2013.01); *A61N 1/39046* (2017.08); *A61N 1/3993* (2013.01)

(56) References Cited

U.S. PATENT DOCUMENTS

| | | | |
|---|---|---|---|
| 4,632,122 A | 12/1986 | Johansson et al. | |
| 4,698,848 A | 10/1987 | Buckley | |
| 4,928,690 A | 5/1990 | Heilman et al. | |
| 4,978,926 A | 12/1990 | Zerod et al. | |
| 5,062,834 A | 11/1991 | Gross et al. | |
| 5,078,134 A | 1/1992 | Heilman et al. | |
| 5,153,584 A | 10/1992 | Engira | |
| 5,176,380 A | 1/1993 | Evans et al. | |
| 5,330,505 A | 7/1994 | Cohen | |
| 5,348,008 A | 9/1994 | Bornn et al. | |
| 5,353,793 A | 10/1994 | Bornn | |
| 5,357,696 A | 10/1994 | Gray et al. | |
| 5,365,932 A | 11/1994 | Greenhut | |
| 5,564,429 A | 10/1996 | Bornn et al. | |
| 5,662,689 A | 9/1997 | Elsberry et al. | |
| 5,718,242 A | 2/1998 | McClure et al. | |
| 5,738,102 A | 4/1998 | Lemelson | |
| 5,741,306 A | 4/1998 | Glegyak et al. | |
| 5,758,443 A | 6/1998 | Pedrazzini | |
| 5,792,190 A | 8/1998 | Olson et al. | |
| 5,929,601 A | 7/1999 | Kaib et al. | |
| 5,944,669 A | 8/1999 | Kaib | |
| 6,016,445 A | 1/2000 | Baura | |
| 6,045,503 A | 4/2000 | Grabner et al. | |
| 6,065,154 A | 5/2000 | Hulings et al. | |
| 6,097,982 A | 8/2000 | Glegyak et al. | |
| 6,097,987 A | 8/2000 | Milani | |
| 6,148,233 A | 11/2000 | Owen | |
| 6,169,387 B1 | 1/2001 | Kaib | |
| 6,169,397 B1 | 1/2001 | Steinbach et al. | |
| 6,253,099 B1 | 6/2001 | Oskin et al. | |
| 6,280,461 B1 | 8/2001 | Glegyak et al. | |
| 6,390,996 B1 | 5/2002 | Halperin et al. | |
| 6,406,426 B1 | 6/2002 | Reuss et al. | |
| 6,666,830 B1 | 12/2003 | Lehrman et al. | |
| 6,681,003 B2 | 1/2004 | Linder et al. | |
| 6,690,969 B2 | 2/2004 | Bystrom et al. | |
| 6,790,178 B1 | 9/2004 | Mault et al. | |
| 6,804,554 B2 | 10/2004 | Ujhelyi et al. | |
| 6,827,695 B2 | 12/2004 | Palazzolo et al. | |
| 6,865,413 B2 | 3/2005 | Halperin et al. | |
| 6,908,437 B2 | 6/2005 | Bardy | |
| 6,980,112 B2 | 12/2005 | Nee | |
| 6,990,373 B2 | 1/2006 | Jayne et al. | |
| 7,074,199 B2 | 7/2006 | Halperin et al. | |
| 7,108,665 B2 | 9/2006 | Halperin et al. | |
| 7,118,542 B2 | 10/2006 | Palazzolo et al. | |
| 7,122,014 B2 | 10/2006 | Palazzolo et al. | |
| 7,149,579 B1 | 12/2006 | Koh et al. | |
| 7,177,684 B1 | 2/2007 | Kroll et al. | |
| 7,220,235 B2 | 5/2007 | Geheb et al. | |
| 7,277,752 B2 | 10/2007 | Matos | |
| 7,295,871 B2 | 11/2007 | Halperin et al. | |
| 7,340,296 B2 | 3/2008 | Stahmann et al. | |
| 7,427,921 B2 | 9/2008 | Van Woudenberg | |
| 7,453,354 B2 | 11/2008 | Reiter et al. | |
| 7,476,206 B2 | 1/2009 | Palazzolo et al. | |
| 7,488,293 B2 | 2/2009 | Marcovecchio et al. | |
| 7,702,390 B1 | 4/2010 | Min | |
| 7,810,172 B2 | 10/2010 | Williams | |
| 7,831,303 B2 | 11/2010 | Rueter et al. | |
| 7,974,689 B2 | 7/2011 | Volpe et al. | |
| 7,991,460 B2 | 8/2011 | Fischell et al. | |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 8,369,944 B2 | 2/2013 | Macho et al. | |
| 8,600,486 B2 | 12/2013 | Kaib et al. | |
| 8,649,861 B2 | 2/2014 | Donnelly et al. | |
| 8,706,215 B2 | 4/2014 | Kaib et al. | |
| 8,904,214 B2 | 12/2014 | Volpe et al. | |
| 8,909,335 B2 | 12/2014 | Radzelovage | |
| 9,008,801 B2 | 4/2015 | Kaib et al. | |
| 9,135,398 B2 | 9/2015 | Kaib et al. | |
| 9,398,859 B2 | 7/2016 | Volpe et al. | |
| 2002/0107435 A1 | 8/2002 | Swetlik et al. | |
| 2003/0004547 A1 | 1/2003 | Owen et al. | |
| 2003/0023277 A1 | 1/2003 | Owen et al. | |
| 2003/0032988 A1 | 2/2003 | Finke | |
| 2003/0095648 A1 | 5/2003 | Kaib et al. | |
| 2003/0128121 A1 | 7/2003 | Nee | |
| 2003/0149462 A1 | 8/2003 | White et al. | |
| 2003/0158593 A1 | 8/2003 | Heilman et al. | |
| 2003/0174049 A1 | 9/2003 | Beigel et al. | |
| 2003/0195567 A1 | 10/2003 | Jayne et al. | |
| 2003/0212311 A1 | 11/2003 | Nova et al. | |
| 2003/0233129 A1 | 12/2003 | Matos | |
| 2004/0007970 A1 | 1/2004 | Ma et al. | |
| 2004/0049233 A1 | 3/2004 | Edwards | |
| 2004/0128310 A1 | 7/2004 | Zmudzinski et al. | |
| 2004/0143297 A1 | 7/2004 | Maynard | |
| 2005/0049515 A1 | 3/2005 | Misczynski et al. | |
| 2005/0131465 A1 | 6/2005 | Freeman et al. | |
| 2005/0177051 A1 | 8/2005 | Almen | |
| 2006/0036292 A1 | 2/2006 | Smith et al. | |
| 2006/0085049 A1 | 4/2006 | Cory et al. | |
| 2006/0129067 A1 | 6/2006 | Grajales et al. | |
| 2006/0178706 A1 | 8/2006 | Lisogurski et al. | |
| 2006/0220809 A1 | 10/2006 | Stigall et al. | |
| 2006/0264776 A1 | 11/2006 | Stahmann et al. | |
| 2006/0270952 A1 | 11/2006 | Freeman et al. | |
| 2007/0073120 A1 | 3/2007 | Li et al. | |
| 2007/0118056 A1 | 5/2007 | Wang et al. | |
| 2007/0129769 A1 | 6/2007 | Bourget et al. | |
| 2007/0161913 A1 | 7/2007 | Farrell et al. | |
| 2007/0169364 A1 | 7/2007 | Townsend et al. | |
| 2007/0239220 A1 | 10/2007 | Greenhut et al. | |
| 2007/0265671 A1 | 11/2007 | Roberts et al. | |
| 2007/0299474 A1 | 12/2007 | Brink | |
| 2008/0004536 A1 | 1/2008 | Baxi et al. | |
| 2008/0004904 A1 | 1/2008 | Fran | |
| 2008/0015454 A1 | 1/2008 | Gal | |
| 2008/0030656 A1 | 2/2008 | Watson et al. | |
| 2008/0031270 A1 | 2/2008 | Tran et al. | |
| 2008/0033495 A1 | 2/2008 | Kumar | |
| 2008/0045815 A1 | 2/2008 | Derchak et al. | |
| 2008/0046015 A1 | 2/2008 | Freeman et al. | |
| 2008/0058884 A1 | 3/2008 | Matos | |
| 2008/0221631 A1 | 9/2008 | Dupelle | |
| 2008/0249591 A1 | 10/2008 | Gaw et al. | |
| 2008/0287770 A1 | 11/2008 | Kurzweil et al. | |
| 2008/0306562 A1* | 12/2008 | Donnelly | A61N 1/3925 607/6 |
| 2008/0312520 A1 | 12/2008 | Rowlandson et al. | |
| 2008/0312709 A1 | 12/2008 | Volpe et al. | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |
| 2009/0076345 A1 | 3/2009 | Manicka et al. | |
| 2009/0076346 A1 | 3/2009 | James et al. | |
| 2009/0076348 A1 | 3/2009 | Manicka et al. | |
| 2009/0076349 A1 | 3/2009 | Libbus et al. | |
| 2009/0076350 A1 | 3/2009 | Bly et al. | |
| 2009/0076363 A1 | 3/2009 | Bly et al. | |
| 2009/0076364 A1 | 3/2009 | Libbus et al. | |
| 2009/0076397 A1 | 3/2009 | Libbus et al. | |
| 2009/0076405 A1 | 3/2009 | Amurthur et al. | |
| 2009/0076410 A1 | 3/2009 | Libbus et al. | |
| 2009/0076559 A1 | 3/2009 | Libbus et al. | |
| 2009/0082691 A1 | 3/2009 | Denison et al. | |
| 2009/0093687 A1 | 4/2009 | Telfort et al. | |
| 2009/0138059 A1 | 5/2009 | Ouwerkerk | |
| 2009/0177100 A1 | 7/2009 | Ternes | |
| 2009/0234410 A1 | 9/2009 | Libbus et al. | |

(56) References Cited

U.S. PATENT DOCUMENTS

| | | |
|---|---|---|
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0083968 A1 | 4/2010 | Wondka et al. |
| 2010/0179438 A1 | 7/2010 | Heneghan et al. |
| 2010/0234715 A1 | 9/2010 | Shin et al. |
| 2010/0234716 A1 | 9/2010 | Engel |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0077728 A1 | 3/2011 | Li et al. |
| 2011/0196220 A1 | 8/2011 | Storm |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0144551 A1 | 6/2012 | Guldalian |
| 2012/0146797 A1 | 6/2012 | Oskin et al. |
| 2012/0158074 A1 | 6/2012 | Hall |
| 2012/0158075 A1 | 6/2012 | Kaib et al. |
| 2013/0325078 A1 | 12/2013 | Whiting et al. |
| 2013/0325096 A1 | 12/2013 | Dupelle et al. |
| 2014/0163334 A1 | 6/2014 | Volpe et al. |
| 2014/0364918 A1 | 12/2014 | Owen et al. |
| 2014/0371806 A1 | 12/2014 | Raymond et al. |
| 2015/0005588 A1 | 1/2015 | Kaib |
| 2015/0037636 A1 | 2/2015 | Amsler et al. |
| 2015/0039053 A1* | 2/2015 | Kaib ............... A61N 1/37258 607/63 |
| 2015/0217121 A1 | 8/2015 | Subramanian et al. |
| 2015/0231403 A1 | 8/2015 | Kaib et al. |
| 2016/0136446 A1* | 5/2016 | Daynes ............. A61N 1/3968 607/5 |
| 2016/0143585 A1 | 5/2016 | Donnelly et al. |
| 2017/0056682 A1* | 3/2017 | Kumar ............... A61N 1/3987 |
| 2017/0143977 A1* | 5/2017 | Kaib ................... A61N 1/046 |
| 2017/0199797 A1* | 7/2017 | Hresko ............... G16H 40/40 |
| 2018/0055442 A1* | 3/2018 | Freeman ............. A61B 5/1118 |
| 2019/0022400 A1 | 1/2019 | Kumar et al. |

FOREIGN PATENT DOCUMENTS

| | | |
|---|---|---|
| CN | 101848677 | 9/2010 |
| DE | 2644236 | 4/1981 |
| EP | 0295497 | 7/1990 |
| EP | 0335356 | 8/1990 |
| EP | 1642616 | 4/2006 |
| EP | 1455640 | 1/2008 |
| EP | 1720446 | 7/2010 |
| EP | 3121225 | 1/2017 |
| EP | 3110503 | 3/2019 |
| JP | S6368135 | 3/1988 |
| JP | 5115450 | 5/1993 |
| JP | H07541 | 1/1995 |
| JP | H10-28679 | 2/1998 |
| JP | H1319119 | 11/1999 |
| JP | 2002102361 | 4/2002 |
| JP | 2002514107 | 5/2002 |
| JP | 2002200059 | 7/2002 |
| JP | 2002534231 | 10/2002 |
| JP | 2003235997 | 8/2003 |
| JP | 2004538066 | 12/2004 |
| JP | 2005275606 | 5/2005 |
| JP | 2007531592 | 11/2007 |
| JP | 2008302228 | 12/2008 |
| JP | 2009510276 | 3/2009 |
| JP | 2009518057 | 5/2009 |
| JP | 2009528909 | 8/2009 |
| JP | 2010508128 | 3/2010 |
| JP | 2010530114 | 9/2010 |
| WO | 200002484 | 1/2000 |
| WO | 2001042384 | 6/2001 |
| WO | 2004054656 | 7/2004 |
| WO | 2004067083 | 8/2004 |
| WO | 2005082454 | 9/2005 |
| WO | 2006050235 | 5/2006 |
| WO | 2007019325 | 2/2007 |
| WO | 20070057169 | 5/2007 |
| WO | 2007077997 | 7/2007 |
| WO | 2008137286 | 11/2008 |
| WO | 2009034506 | 3/2009 |
| WO | 2010014497 | 2/2010 |
| WO | 2010025432 | 3/2010 |
| WO | 20140210510 | 12/2014 |
| WO | 2015127466 | 8/2015 |
| WO | 20160149583 | 9/2016 |
| WO | 2017035502 | 3/2017 |

OTHER PUBLICATIONS

Harnett, P.R. et al., "A Survey and Comparison of Laboratory Test Methods for Measuring Wicking", Textile Research Journal, Jul. 1984.

MDPI Open Access Publishing, Coatings | Special Issue : Fabric Coatings, http://www.mdpi.com/journal/coating/special_issues/fabric-coatings, Jul. 3, 2018, 7 pages.

Tebrake, Maggie G., "Selecting the right medical adhesive tape—Challenges facing the medical devise designer", 3M Medical OEM, www.3M.co.uk/medicaloem, 2014, 16 pages.

\* cited by examiner

WEARABLE MEDICAL DEVICE RESPONSE MECHANISMS AND METHODS OF USE

CROSS-REFERENCE TO RELATED APPLICATIONS

This application claims priority under 35 U.S.C. § 119(e) to U.S. Provisional Patent Application Ser. No. 62/785,805 filed Dec. 28, 2018, titled "Wearable Medical Device Response Mechanisms And Methods Of Use," the entirety of which is hereby incorporated by reference.

BACKGROUND

The present disclosure is directed to wearable cardiac monitoring and treatment devices.

A patient suffering from heart failure experiences symptoms caused by a weak or damaged heart contracting inefficiently and failing to pump effectively to circulate oxygenated blood through the body. A heart may be weakened by, for example, abnormal heart rhythms (e.g., heart arrhythmias), high blood pressure, coronary artery disease, myocardial infarction, and myocarditis.

Left untreated, heart failure could lead certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia.

Cardiac arrest can occur when various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for supporting life. It is generally useful to monitor heart failure patients in order to assess heart failure symptoms early and provide interventional therapies as soon as possible.

Wearable cardiac monitoring and treatment devices are provided to monitor for such arrhythmias and provide a treatment when a life-threatening arrhythmia is detected. Such devices are worn by the patient continuously to provide constant protection. As such, the devices need to be designed to be comfortable and easy to use.

SUMMARY

In one example, a system for providing a patient with arrhythmia treatment that is worn partially under clothing of the patient includes an arrhythmia monitoring and treatment assembly configured to be worn on a torso of the patient and discreetly extend from a skin surface of the patient. The arrhythmia monitoring and treatment assembly is configured for providing therapy to the patient on detecting one or more arrhythmia conditions of the patient. The system includes a first at least one user response button is disposed on the arrhythmia monitoring and treatment assembly at a first location on the patient's torso such that the first at least one user response button is concealed under the clothing of the patient. The system includes a second at least one user response button is configured to be worn on a second location of the patient's body at a location other than the torso such that the second at least one user response button is accessible to the patient. The system includes a processor disposed in the arrhythmia monitoring and treatment assembly is configured to analyze an ECG signal of the patient received via the arrhythmia monitoring and treatment assembly to detect the one or more arrhythmia conditions of the patient, cause the arrhythmia monitoring and treatment assembly to provide a warning of an impending therapy to be delivered to the patient in response to a detected one or more arrhythmia conditions of the patient, receive from at least one of the first and second at least one user response buttons a user input in response to the warning of the impending therapy, and cause the arrhythmia monitoring and treatment assembly to suspend the impending therapy.

Implementations of the system may include one or more of the following features.

In examples, the arrhythmia monitoring and treatment assembly includes a housing having a tallest height extending no more than 10 cm from the skin surface of the patient.

In examples, the arrhythmia monitoring and treatment assembly includes at least one pad configured to be adhesively attached to the patient's torso, and the housing is mounted on the at least one pad.

In examples, the arrhythmia monitoring and treatment assembly includes a first pad configured to be adhesively attached to the patient's torso, and a second pad configured to be adhesively attached to the patient's torso, and the housing is mounted on the first pad.

In examples, the first pad includes a first at least one therapy electrode and a first at least one sensing electrode, the second pad includes a second at least one therapy electrode and a second at least one sensing electrode, and the processor is configured to receive the ECG signal sensed from the first and second at least one sensing electrodes, and provide the therapy to the patient via the first and second at least one therapy electrodes.

In examples, the first at least one user response button disposed on the arrhythmia monitoring and treatment assembly and the second at least one user response button are configured to be worn by the patient simultaneously.

In examples, the system includes a wearable article. The wearable article can include the second at least one user response button, and communications circuitry configured to transmit information relating to the user input from the second at least one user response button to the processor disposed in the arrhythmia monitoring and treatment assembly. In examples, the wearable article includes at least one of a bracelet, a ring, a retractable pendant, a necklace, a belt configured to be worn over the clothing, a sash configured to be worn over the clothing, a bolo tie, a watch, an arm band, and a patch configured to be worn over the clothing of the patient at an accessible location. In examples, the wearable article is configured to be at least partially disposed under the clothing of the patient.

In examples, the communications circuitry is configured to provide the information relating to the user input from the second at least one user response button via a wireless communications protocol. The second at least one user response button can be uniquely paired with the arrhythmia monitoring and treatment assembly. In examples, the wireless communications protocol is at least one of Wi-Fi, BLUETOOTH, broadband cellular, and/or Long-Term Evolution (LTE), GSM/EDGE, and UMTS/HSPA.

In examples, a wired link extends between the arrhythmia monitoring and treatment assembly and the wearable article such that the communications circuitry and the processor are in wired communication. The wired link can be configured to be detachable from one or both of the arrhythmia monitoring and treatment assembly and the wearable article. In examples, at least one of the arrhythmia monitoring and treatment assembly and the wearable article further comprises a retractable spool and pawl configured to adjust a length of the wired link.

In examples, the wearable article includes one or more sensors configured to verify an identity of the patient based on at least one of audible, touch-based, signal-based, and visible information, and delay therapy delivery based at least in part on the verified identity.

In examples, the second at least one user response button includes at least one of a mechanically-actuatable button, a touch screen interface, and at least one touch screen button.

In examples, the arrhythmia monitoring and treatment assembly includes a housing and the first at least one user response button is disposed on the housing and is raised or depressed relative to a surface of the housing so as to be palpable beneath one or more layers of the clothing.

In examples, the arrhythmia monitoring and treatment assembly further includes a plurality of ECG sensing electrodes and associated circuitry configured to monitor the ECG signal of the patient, and a plurality of therapy electrodes and an associated therapy delivery circuit configured to deliver the therapy to the patient. A garment is configured to be worn about the torso of the patient to couple the arrhythmia monitoring and treatment device to the torso of the patient such that on delivering the therapy, one or more defibrillation or pacing pulses discharge into the torso via the plurality of therapy electrodes.

In one example, a system for providing a patient with arrhythmia treatment is worn partially under clothing of the patient and includes an arrhythmia monitoring and treatment assembly configured to be worn on a torso of the patient. The arrhythmia monitoring and treatment assembly has a housing extending between at least around 1 cm to around 10 cm from a skin surface of the patient, and the arrhythmia monitoring and treatment assembly is configured for providing therapy to the patient on detecting one or more arrhythmia conditions of the patient. The system includes a first at least one user response button disposed on the arrhythmia monitoring and treatment assembly at a first location on the patient's torso such that the first at least one user response button is concealed under clothing of the patient, and a second at least one user response button configured to be worn on a second location of the patient's body at a location other than the torso such that the second at least one user response button is accessible to the patient. The system includes a processor disposed in the arrhythmia monitoring and treatment assembly configured to analyze an ECG signal of the patient received via the arrhythmia monitoring and treatment assembly to detect the one or more arrhythmia conditions of the patient, cause the arrhythmia monitoring and treatment assembly to provide a warning of an impending therapy to be delivered to the patient in response to a detected one or more arrhythmia conditions of the patient, receive from at least one of the first and second at least one user response buttons a user input in response to the warning of the impending therapy, and cause the arrhythmia monitoring and treatment assembly to suspend the impending therapy.

Implementations of the system may include one or more of the following features.

In examples, the housing of the arrhythmia monitoring and treatment assembly extends from the skin surface of the patient in a range of 2 to 9 cm.

In examples, the housing of the arrhythmia monitoring and treatment assembly extends from the skin surface of the patient in a range of 4 to 7 cm.

In examples, a longest axis of the arrhythmia monitoring and treatment assembly is in a range of between 2 to 20 times longer than a tallest height of the housing from the skin surface.

In examples, a vertical side profile of the arrhythmia monitoring and treatment assembly is asymmetrical about one or both of a horizontal axis and a vertical axis. In examples, a tallest height of the arrhythmia monitoring and treatment assembly from the skin surface is disposed lower on the torso than a shortest height of the arrhythmia monitoring and treatment assembly from the skin surface. A ratio of the tallest height to the shortest height can be in a range from 10:1 to 2:1.

In examples, the arrhythmia monitoring and treatment assembly covers between about 10% and 70% of a total surface area of the torso of the patient.

In one example, a system for providing a patient with arrhythmia treatment is worn partially under clothing of the patient and includes an arrhythmia monitoring and treatment assembly configured to be worn on a torso of the patient. The assembly includes an asymmetrical housing having a tallest height extending no more than 10 cm from a skin surface of the patient. The arrhythmia monitoring and treatment assembly is configured for providing therapy to the patient on detecting one or more arrhythmia conditions of the patient. The system includes a first at least one user response button disposed on the arrhythmia monitoring and treatment assembly at a first location on the patient's torso such that the first at least one user response button is concealed under clothing of the patient, and a second at least one user response button configured to be worn on a second location of the patient's body at a location other than the torso such that the second at least one user response button is accessible to the patient. The system includes a processor disposed in the arrhythmia monitoring and treatment assembly configured to analyze an ECG signal of the patient received via the arrhythmia monitoring and treatment assembly to detect the one or more arrhythmia conditions of the patient, cause the arrhythmia monitoring and treatment assembly to provide a warning of an impending therapy to be delivered to the patient in response to a detected one or more arrhythmia conditions of the patient, receive from at least one of the first and second at least one user response buttons a user input in response to the warning of the impending therapy, and cause the arrhythmia monitoring and treatment assembly to suspend the impending therapy.

Implementations of the system may include one or more of the following features.

In examples, the housing of the arrhythmia monitoring and treatment assembly extends from the skin surface of the patient in a range of 2 to 9 cm.

In examples, the housing of the arrhythmia monitoring and treatment assembly extends from the skin surface of the patient in a range of 4 to 7 cm.

In examples, a vertical side profile of the arrhythmia monitoring and treatment assembly is asymmetrical about one or both of a horizontal axis and a vertical axis. In examples, the tallest height of the arrhythmia monitoring and treatment assembly from the skin surface is disposed lower on the torso than a shortest height of arrhythmia monitoring and treatment assembly from the skin surface. In examples, a ratio of the tallest height to the shortest height is in a range from 10:1 to 2:1. In examples, the asymmetrical housing includes at least one of one or more batteries and one or more capacitors disposed within a portion of the housing having the tallest height. In examples, the one or more batteries have a combined envelope volume of one quarter or less than a volume bounded by the housing of the arrhythmia monitoring and treatment assembly and the skin surface of the patient. The one or more batteries can have a capacity in a range of 200-8000 mAh.

In one example, a system for providing a patient with arrhythmia treatment is worn partially under clothing of the patient and includes an arrhythmia monitoring and treatment assembly configured to be worn on a torso of the patient. The arrhythmia monitoring and treatment assembly includes a housing having a tallest height extending no more than 10 cm from a skin surface of the patient. The arrhythmia monitoring and treatment assembly is configured for providing therapy to the patient on detecting one or more arrhythmia conditions of the patient. The arrhythmia monitoring and treatment assembly includes a flexible skin interface layer configured to engage the skin surface of the patient, and a longest axis of the arrhythmia monitoring and treatment assembly is in a range of between 2 to 20 times longer than the tallest height of the housing from the skin surface. The system includes a first at least one user response button disposed on the arrhythmia monitoring and treatment assembly at a first location on the patient's torso such that the first at least one user response button is concealed under clothing of the patient, and a second at least one user response button configured to be worn on a second location of the patient's body at a location other than the torso such that the second at least one user response button is accessible to the patient. The system includes a processor disposed in the arrhythmia monitoring and treatment assembly configured to analyze an ECG signal of the patient received via the arrhythmia monitoring and treatment assembly to detect the one or more arrhythmia conditions of the patient, cause the arrhythmia monitoring and treatment assembly to provide a warning of an impending therapy to be delivered to the patient in response to a detected one or more arrhythmia conditions of the patient, receive from at least one of the first and second at least one user response buttons a user input in response to the warning of the impending therapy, and cause the arrhythmia monitoring and treatment assembly to suspend the impending therapy.

Implementations of the system may include one or more of the following features.

In examples, the flexible skin interface layer includes a rubber and an elastomer having a ratio in a range of 9:6 to 4:1, and the flexible skin interface layer is configured to stretch and bend with the skin of the patient.

In examples, a vertical side profile of the arrhythmia monitoring and treatment assembly is asymmetrical about one or both of a horizontal axis and a vertical axis. In examples, the tallest height of the housing from the skin surface is disposed lower on the torso than a shortest height of the housing. A ratio of the tallest height to the shortest height can be in a range from 10:1 to 2:1.

In examples, the arrhythmia monitoring and treatment assembly covers between about 10% and 70% of a total surface area of the torso of the patient. In examples, the flexible skin interface layer traces a continuous circumferential path about the torso of the patient in a range of 90 degrees to 360 degrees.

In examples, 10 percent to 90 percent of the flexible skin interface layer is covered with one or more components of the monitoring and treatment assembly, and the remaining 90 to 10 percent of the flexible skin interface layer extends beyond a perimeter traced around the one or more components.

In one example, a system for providing a patient with arrhythmia treatment is worn partially under clothing of the patient. The system includes an arrhythmia monitoring and treatment assembly configured to be worn on a torso of the patient and discreetly extending from a skin surface of the patient. The arrhythmia monitoring and treatment assembly is configured for providing therapy to the patient on detecting one or more arrhythmia conditions of the patient. The system includes a first at least one user response button disposed on the arrhythmia monitoring and treatment assembly at a first location on the patient's torso such that the first at least one user response button is concealed under clothing of the patient, and a second at least one user response button configured to be worn on a second location of the patient's body at a location other than the torso such that the second at least one user response button is accessible to the patient. The system includes a processor disposed in the arrhythmia monitoring and treatment assembly. The processor is configured to analyze an ECG signal of the patient received via the arrhythmia monitoring and treatment assembly to detect the one or more arrhythmia conditions of the patient, cause the arrhythmia monitoring and treatment assembly to provide a warning of an impending therapy to be delivered to the patient in response to a detected one or more arrhythmia conditions of the patient, receive from at least one of the first and second at least one user response buttons a user input in response to the warning of the impending therapy, and cause the arrhythmia monitoring and treatment assembly to suspend the impending therapy.

In examples, arrhythmia monitoring and treatment assembly further includes a plurality of ECG sensing electrodes and associated circuitry configured to monitor the ECG signal of the patient, and a plurality of therapy electrodes and an associated therapy delivery circuit configured to deliver the therapy to the patient. In examples, the processor is coupled to the plurality of ECG sensing electrodes and the associated circuitry configured to monitor the ECG signal of the patient and the plurality of therapy electrodes and associated therapy delivery circuit. The processor is further configured to analyze the ECG signal of the patient received via the plurality of ECG sensing electrodes and detect one or more treatable arrhythmias based on the ECG signal, cause the therapy delivery circuit to deliver, via the plurality of therapy electrodes, one or more defibrillation pulses to the patient on detecting the one or more treatable arrhythmias, and cause the plurality of therapy electrodes to withhold one or more defibrillation pulses to the patient on receiving the user input in response to the warning of the impending therapy.

Implementations of the system may include one or more of the following features.

In examples, the system further includes a garment configured to be worn about the torso of the patient to couple the arrhythmia monitoring and treatment device to the torso of the patient such that on delivering the therapy, one or more defibrillation or pacing pulses discharge into the torso via the plurality of therapy electrodes.

In examples, the plurality of ECG sensing electrodes and the plurality of therapy electrodes are integrated into a first pad configured to be coupled to the torso of the patient. The first pad can include a pressure sensitive adhesive configured for coupling the first pad to the torso of the patient. In examples, the system further includes a second pad configured to be coupled to the torso of the patient and at least one therapy electrode integrated with the second pad. The at least one therapy electrode integrated with the second pad can be in wired communication with the therapy delivery circuit.

In examples, the first at least one user response button disposed on the arrhythmia monitoring and treatment assembly and the second at least one user response button are configured to be worn by the patient simultaneously.

In examples, the system further includes a wearable article. The second at least one user response button is provided by the wearable article, and the wearable article further includes communications circuitry configured to transmit the user input from the second at least one user response button to the processor disposed in the arrhythmia monitoring and treatment assembly. In examples, the wearable article includes at least one of a bracelet, a ring, a retractable pendant, a necklace, a belt configured to be worn over the clothing, a sash configured to be worn over the clothing, a bolo tie, a watch, an arm band, or a patch configured to be worn over the clothing of the patient at an accessible location.

In examples, the wearable article is configured to be at least partially disposed under the clothing of the patient.

In examples, the processor and the second at least one user response button are in wireless communication.

In examples, the second at least one user response button is uniquely paired with the arrhythmia monitoring and treatment assembly.

In examples, the system further includes a wired link extending between the arrhythmia monitoring and treatment assembly and the wearable article such that the communications circuitry and the processor are in wired communication. The wired link can be configured to be detachable from one or both of the arrhythmia monitoring and treatment assembly and the wearable article. At least one of the arrhythmia monitoring and treatment assembly and the wearable article can further include a retractable spool and pawl configured to adjust a length of the wired link.

In examples, the wearable article further includes one or more sensors configured to verify an identity of the patient based on at least one of audible, touch-based, signal-based, and visible information, and delay therapy delivery based at least in part on the verified identity. At least one of the arrhythmia monitoring and treatment device and the wearable article can further include a video camera configured to detect the visible information associated with the patient. In examples, the system can further include a 3D laser ranging sensor in communication with the video camera and configured for at least one of feature recognition and gesture detection. In examples, touch-based information includes at least one of one or more touches on the wearable article, patient fingerprint detection, and repeated taps. In examples, the signal-based information includes at least one of an ECG signal detection and biometric sensing. In examples, the audible information includes at least one of voice recognition and receipt of a pass code or phrase.

In examples, the first at least one user response button includes one or more tactile response buttons disposed on a housing of the arrhythmia monitoring and treatment assembly so that the first at least one user response button is locatable through one or more layers of clothing. The first at least one user response button can be disposed on the housing and raised or depressed relative to a surface of the housing so as to be palpable beneath the one or more layers of clothing.

In examples, the wearable article further includes at least one of a mechanically-actuatable button, a touch screen interface, and at least one touch screen button.

In one example, a method of treating a cardiac arrhythmia includes providing an arrhythmia monitoring and treatment device configured to be worn on a torso of a patient so as to be at least partially concealed under clothing of the patient. The device is configured for providing therapy to the patient on detecting one or more arrhythmia conditions of the patient, and includes a plurality of ECG sensing electrodes and associated circuitry configured to monitor an ECG signal of the patient. The device includes a first at least one user response button disposed on the device at a first location on the patient's torso such that the first at least one user response button is concealed under clothing of the patient, and a processor in communication with the first at least one user response button and the plurality of ECG sensing electrodes and associated circuitry. The method includes providing a second at least one user response button configured to be worn on a second location of the patient's body at a location other than the torso such that the second at least one user response button is accessible to the patient, the second at least one user response button being in communication with the processor. The method includes analyzing, by the processor, the ECG signal of the patient received via the device to detect the one or more arrhythmia conditions of the patient, causing, by the processor, the device to provide a warning of an impending therapy to be delivered to the patient in response to a detected one or more arrhythmia conditions of the patient, receiving, at the processor, from at least one of the first and second at least one user response buttons a user input in response to the warning of the impending therapy, and causing, by the processor, the device to suspend the impending therapy.

DETAILED DESCRIPTION

This disclosure relates to a cardiac monitoring and treatment system that detects one or more arrhythmias based on physiological signals from a patient. The system is worn at least partially under clothing. The arrhythmias include those that may be treated by defibrillation pulses, such as ventricular fibrillation (VF) and shockable ventricular tachycardia (VT), or by one or more pacing pulses, such as bradycardia, tachycardia, and asystole. A system as disclosed herein includes an arrhythmia monitoring and treatment assembly worn under clothing. A system as disclosed herein includes an article worn by the patient that is in communication with the arrhythmia monitoring and treatment assembly. For example, the article is disposed on a readily accessible location on the patient's body. In implementations, both the arrhythmia monitoring and treatment assembly and the readily accessible worn article include patient input features for communicating with and providing controlling input to the system. Such communication can include, for example, a patient input that delays or prevents delivery of a treatment, such as a defibrillation or pacing shock. In some implementations, the arrhythmia monitoring and treatment assembly includes a wearable medical device adhesively coupled to a patient. The wearable medical device monitors the patient's physiological conditions, e.g., cardiac signals, respiratory parameters, and patient activity, and delivers potentially life-saving treatment to the patient. Embodiments of the arrhythmia monitoring and treatment assembly can include garments or wearable supports for supporting one or more components on a patient's torso, components adhesively coupled to the torso of a patient, or some combination of adhesively coupled components and garments or wearable supports.

Figure 1A:
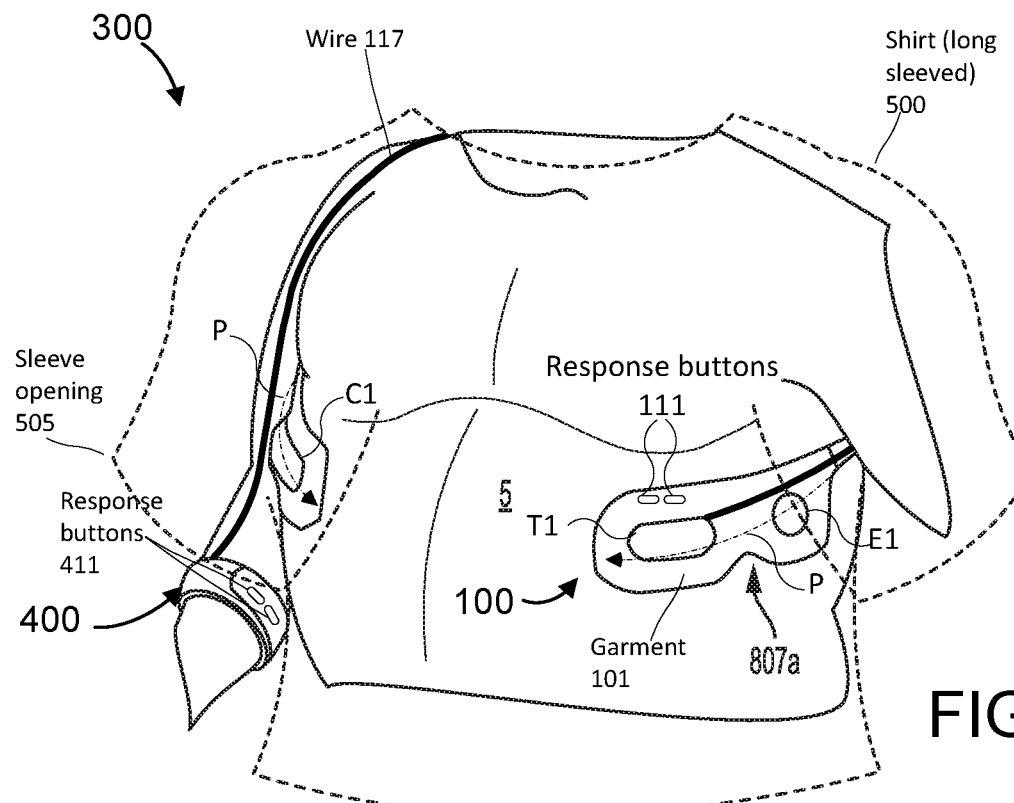
FIG. 1A depicts a schematic front view of an example wearable cardiac monitoring and treatment system including a wearable device and a wearable article.
Figure 1B:
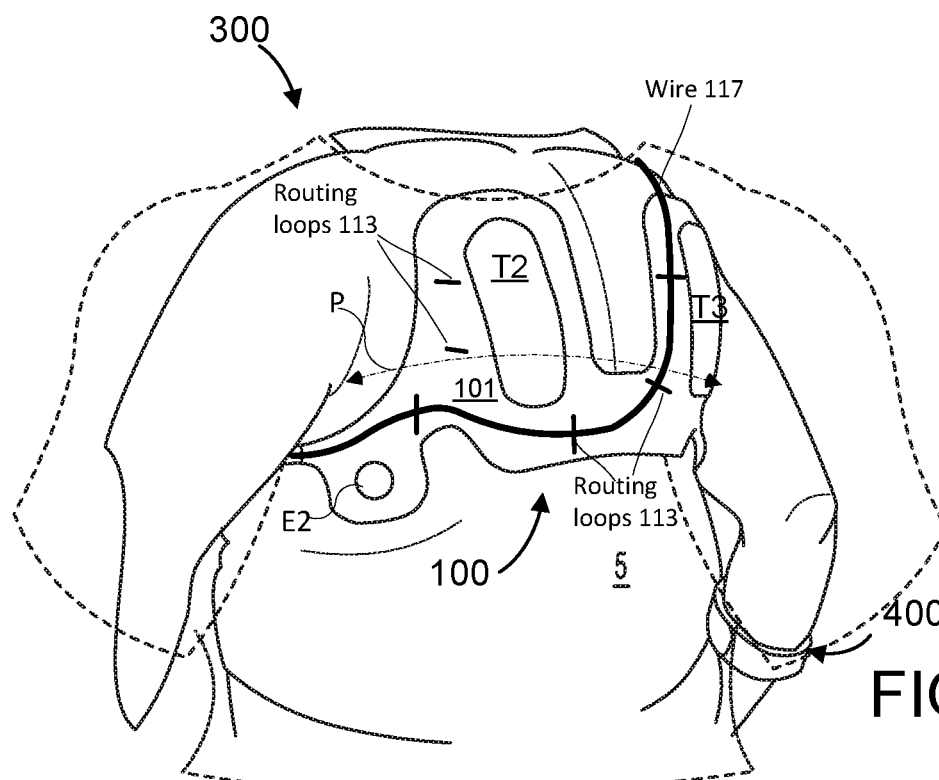
FIG. 1B depicts a schematic rear view of an example wearable cardiac monitoring and treatment system including a wearable device and a wearable article.

As shown in FIGS. 1A-B, in implementations the system 300 includes a wearable arrhythmia monitoring and treatment assembly that is as a patient worn cardiac monitoring and treatment device 100. The device 100 is configured to be worn on the torso 5 of the patient and discreetly extend from the skin surface of the patient under clothing (e.g., a shirt 500) worn over the device 100. In some implementations, such as that of FIGS. 1A-B, various components of the device 100 are disposed about the torso 5 of the patient to reduce the bulk of any one component or a plurality of collocated components. The various treatment and monitoring components can be adhesively coupled and/or held against the torso of the patient by a garment, such as a support structure 101. In some embodiments, the support structure 101 is an adhesively coupled pad holding the monitoring and treatment components against the skin of the patient. In other embodiments, the structure is a compression garment and/or other vestment including closure mechanisms for securing the wearable medical device 100 about the torso 5 of the patient.

In implementations, the support structure 101 is a flexible skin interface layer configured to engage the skin surface of the patient and support a plurality of treatment and monitoring components of the wearable medical device 100. In implementations, the flexible skin interface layer is a supple substrate configured to stretch and bend with the skin of the patient. In implementations the flexible skin interface layer includes at least a rubber and an elastomer having a ratio in a range of 9:6 to 4:1. In implementations, the wearable medical device 100 is an arrhythmia monitoring and treatment assembly covering between about 10% and 70% of the total surface area of the torso 5 of the patient. By preventing a volumetric aggregation of many components at a single location on the support structure 101, the wearable medical device 100 presents with a low profile overall, such as the implementation of FIGS. 1A-B having a low profile, wrap-around style support structure 101. As shown in FIGS. 1A and 1B, in implementations, the device 100 includes a support structure 101 (e.g., a flexible skin interface layer) that traces a continuous circumferential path P about the torso 5 of the patient. In implementations, the circumferential path P covers a range of 90 degrees to 360 degrees of the circumference of the patient's torso 5. In implementations, 10 percent to 90 percent of the flexible skin interface layer is covered with one or more treatment and monitoring components (e.g., T1-T3, E1-E2, C1) of the wearable medical device 100 and the remaining 90 to 10 percent extends beyond the perimeter of the one or more monitoring components. Covering more of the torso 5 with the flexible skin interface layer enables the components to be distributed more individually or in smaller, less volumetric aggregations at various positions along the support structure 101. This aids in weight distribution and increased comfort to the patient during a prescribed duration of wear while also providing a discreet appearance more closely following the natural contours of the patient's body.

As shown in the implementation of FIGS. 1A-B, the system includes a wearable article 400 in communication with the device 100. A first at least one user response button 111 is disposed on the wearable medical device 100, and a second at least one user response button 411 is configured to be worn on a second location of the patient's body at a location other than the torso 5 such that the second at least one user response button 411 is readily accessible to the patient. In the example of FIGS. 1A-B, the wearable article 400 is a wrist worn device worn at or near a sleeve opening 505 of a shirt 500 worn over the low-profile device 100. Such wrist worn articles 400 can resemble and/or also function as commonly worn devices such as a watch, a bracelet, or fitness device. In this regard, the wearable article 400 can be configured to be secured about the forearm of the patient (e.g., between the patient's wrist area and below the elbow). As such, patients that wear short sleeved clothing would be able to readily access the wearable article 400. In an implementation, the wearable article 400 is configured to be secured around a wrist area of the patient's forearm.

The wearable article 400 can be worn on either the dominant or the non-dominant arm. For example, the patient may choose to wear the article 400 on a dominant arm, for example, to ensure faster and/or reliable access to the article 400 in the event of a cardiac emergency than when worn on a non-dominant arm. In implementations, the device 100 includes one or more routing eyelets 113 or loops for directing a wire 117 connecting the device 100 to a wearable article 400 on either arm. In implementations, the routing loops are affixed to the support structure 101 so that the wire 117 can be optionally threaded in one direction or another over a preferred shoulder. In other implementations, the device 100 may include a bi-directional retention element. For example, this bi-directional element can include a single, centrally located loop engaged with the support structure 101 at a ball joint enabling a patient to quickly and easily maneuver the wire 117 over one shoulder or another to route the wearable article 400 to a preferred side of the body, e.g. a left arm or a right arm.

In implementations, a processor disposed in the device 100 is configured to analyze an ECG signal of the patient received via the device 100 to detect one or more arrhythmia conditions of the patient. In response to detecting one or more arrhythmia conditions, the processor is configured to cause the device 100 to provide a warning of an impending therapy to be delivered to the patient. Responsive to the warning of the impending therapy, the patient may then suspend the therapy by touching and/or pressing at least one of the first at least one user response button 111 and second at least one user response button 411. Such action(s) can cause a command to be conveyed to the processor of device 100 to suspend the therapy. Because the device 100 is worn under clothing, such as a shirt 500, the second at least one user response button 411 provides the patient with a readily accessible interface for communicating with the device 100 at the sounding of an impending treatment alarm. In the embodiment of FIGS. 1A-B, the wearable article 400 is in wired communication with the device 100 (e.g., via a wire 117 extending from the device 100 to the wearable article 400). In other implementations, as will be described subsequently, the wearable article 400 can be in wireless communication with a processor of the device 100 for transmitting a user instruction to delay therapy.

If a patient's detected cardiac arrhythmia condition has stabilized or improved and the patient is conscious, the patient may delay the treatment that would otherwise modify the rhythm of their heart. Having the second at least one user response button 411 provided on a housing or user interface touch screen of a wearable article 400 enables a patient to readily delay a treatment. In implementations, the wearable article 400 is a commonly worn and familiar article. This further enhances the discreet appearance of the system 300, thereby aiding in patient compliance with wearing the system 300 as prescribed by a physician for a continuous short term or long term duration. In implementations, the second at least one user response button includes two buttons so that, by design, the patient presses the two buttons simultaneously with two fingers. This two finger configuration assists with preventing accidental bumps and button presses to a single button during the sounding of an imminent therapy alert. In other configurations, the second at least one user response button may include only a single response button. In such configurations, the patient is prompted to provide a confirming user input to verify that a button press was intentional. Mechanisms for detecting intentional input to the second one or more user response buttons will be discussed subsequently with regard to implementations of the system 300 and are applicable to all implementations described herein.

Figure 2:
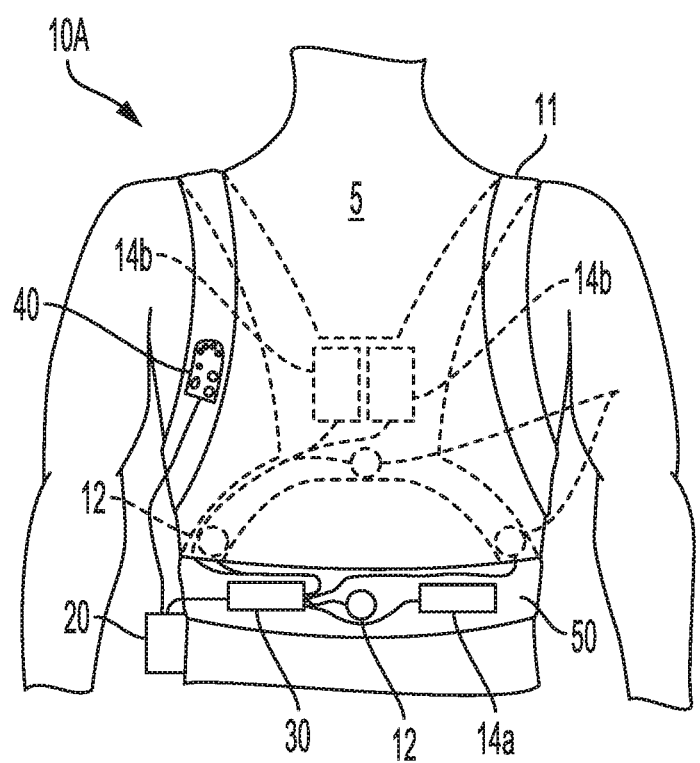
FIG. 2 depicts a schematic of an example wearable cardiac monitoring and treatment device including a wearable support.

As described in U.S. Pat. No. 8,983,597, titled "MEDICAL MONITORING AND TREATMENT DEVICE WITH EXTERNAL PACING," issued on Mar. 17, 2015 (hereinafter the "'597 patent"), which is incorporated herein by reference in its entirety, an example patient worn cardiac monitoring and treatment device can be, for example, an ambulatory medical device that is capable of and designed for moving with the patient as the patient goes about his or her daily routine. For example, as shown in FIG. 2, the ambulatory medical device 10A can be a wearable cardioverter defibrillator (WCD) and can include one or more of the following: a garment 11, one or more physiological sensors 12 (e.g., ECG electrodes, heart rate sensors, vibrational sensors, and/or other physiological sensors), one or more therapy electrodes 14a and 14b (collectively referred to herein as therapy electrodes 14), a medical device controller 20, a connection pod 30, a patient interface pod 40, a belt 50 about the patient's torso to support one or more components, or any combination of these. In some examples, at least some of the components of the medical device 10A can be configured to be affixed to the garment 11 (or in some examples, permanently integrated into the garment 11), which can be worn about the patient's torso 5.

The medical device controller 20 can be operatively coupled to the physiological sensors 12 which can be affixed to the garment 11, e.g., assembled into the garment 11 or removably attached to the garment 11, e.g., using hook and loop fasteners. In some implementations, the physiological sensors 12 can be permanently integrated into the garment 11. The medical device controller 20 can be operatively coupled to the therapy electrodes 14. For example, the therapy electrodes 14 can also be assembled into the garment 11, or, in some implementations, the therapy electrodes 14 can be permanently integrated into the garment 11.

In embodiments according to this disclosure, such as that of FIGS. 3-5D, one or more portions of the garment 11 of the device 10A of FIG. 2 can be eliminated, such as such as a holster portion, and the remaining portions combined with other attachment mechanisms. In embodiments, eliminating one or more portions of the garment 11 results in leaving a wearable support configured with relatively less surface area. Such a wearable support can be, for example, a shoulder strap, a vest, a belt, a harness, a bandeau, and/or a sash. In implementations, the wearable support can be fitted to the body as a lightweight stretchable support garment, or other structure for supporting heavier components of the device 10B-G. In one example, the wearable support may be a belt 50 or sash 53, as shown in FIGS. 3 through 5D. The belt 50 or sash 53 is configured to support heavy components of the device 10B-G while other components, such as therapy electrodes 14 and sensors 12 (e.g., ECG sensors), can be adhesively attached to the torso 5 of the patient.

Figure 3:
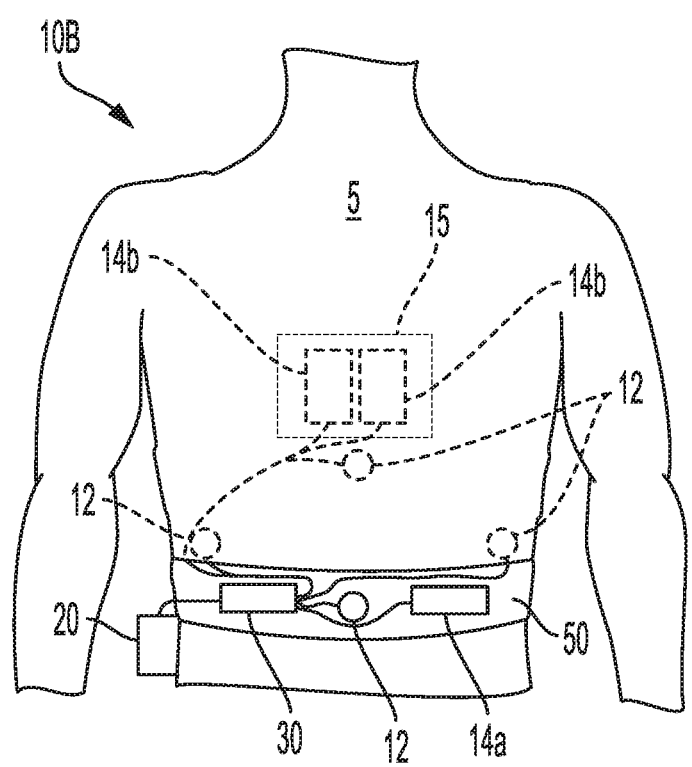
FIG. 3 depicts a schematic of an example wearable cardiac monitoring and treatment device including a wearable support and adhesively coupled portions.

In one example, as shown in FIG. 3, posterior placed therapy electrodes 14b can be integrated into and/or adhered to the patient's skin by an adhesive patch 15 surrounding some or all of the therapy electrodes 14b. The patch can provide an adhesive border for attaching the covered and/or integrated one or more therapy electrodes 14b to the torso 5 of the patient. Heavier components disposed on the wearable support, a belt 50, can include a medical device controller 20 including high voltage components such as one or more batteries, one or more capacitors, one or more circuit boards, one or more controllers and one or more user interfaces. In this example, an anterior placed therapy electrode 14a may also be integrated into or attached to the belt 50. By providing support in the form of a belt 50, for example, the device 10B can retain the heavier components on the lower torso of the patient in an bodily region more capable of supporting additional weight without disrupting a patient's balance or causing musculature soreness of the upper torso. In distributing weight in this way, the device 10B thereby encourages patient compliance with prescribed wear durations by avoiding weight-related discomfort.

Figure 4A:
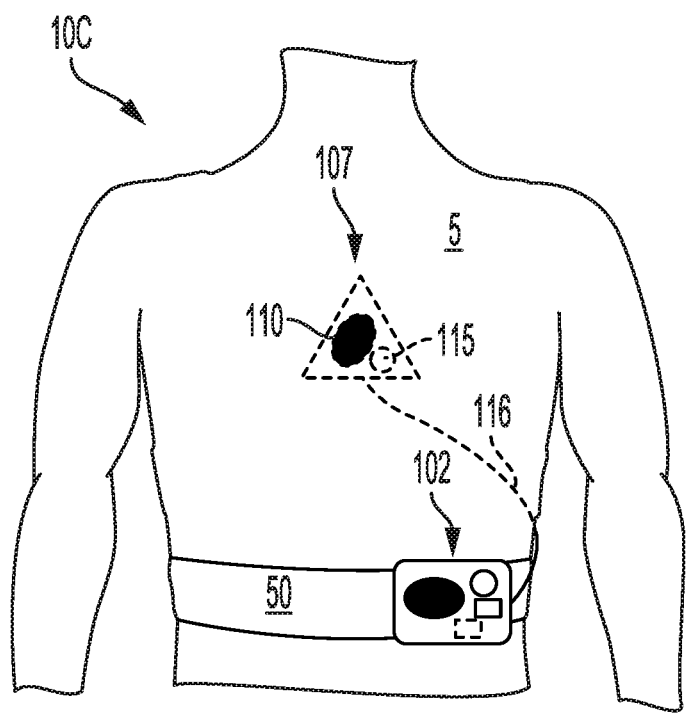
FIG. 4A depicts a schematic of an example wearable cardiac monitoring and treatment device including a wearable support and adhesively coupled portions.
Figure 4B:
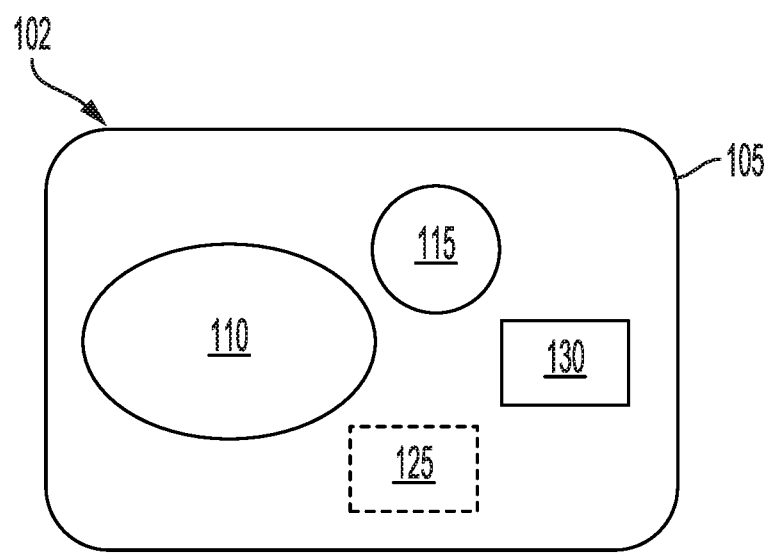
FIG. 4B depicts a plan view schematic of a portion of the example wearable cardiac monitoring and treatment device of FIG. 4A.
Figure 4C:
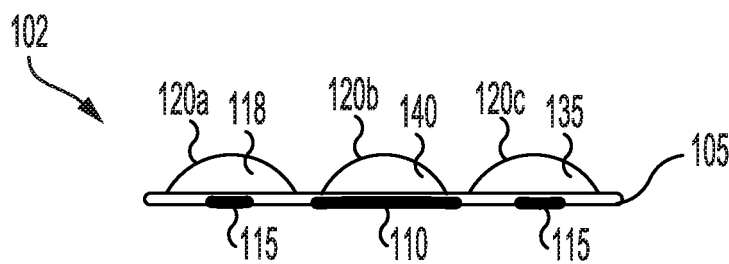
FIG. 4C depicts a side cross-section view of a portion of the example wearable cardiac monitoring and treatment device of FIG. 4B.

Such compliance can be further encouraged by minimizing volume and weight of one or more components to minimize or eliminate any skin irritation associated with surface area contact and/or weight-based forces. For example, as shown in FIGS. 4A through 4C, in embodiments, the device 10C includes a first assembly 102 secured by a belt 50 to a lower left anterior position on the torso 5 and a second assembly 107 in wired connection with the first assembly 102. The second assembly 107 can adhesively secure to an upper posterior torso position, generally between the shoulder blades of the patient. As shown in FIGS. 4B and 4C, the first assembly can include a first pad 105 and one or more therapy electrodes 110 and/or a plurality of ECG sensing electrodes 115 integrated with the pad 105. The first assembly can include a plurality of housings 120a, 120b, 120c, collectively referred to as housings 120. Each housing 120 is configured to form a watertight seal with the pad 105. As previously described with regard to implementations, the pad 105 can be a flexible skin interface layer configured to engage the skin surface of the patient and support a plurality of treatment and monitoring components of the wearable medical device 100. In implementations, the pad 105 is a flexible skin interface layer configured to stretch and bend with the skin of the patient. In implementations the pad 105 includes at least a rubber and an elastomer having a ratio in a range of 9:6 to 4:1. In certain implementations, the housings 120 can extend between around 1 cm and 5 cm from a surface of the pad 105. The housings 120 can include at least an ECG acquisition and conditioning circuit, a therapy delivery circuit, a processor 118, one or more capacitors 135 and one or more batteries 140. In implementations, the second assembly 107 can include only relatively lighter components (e.g., the second assembly weighing around 10-500 grams) such as one or more therapy electrodes 110 and/or one or more ECG sensing electrodes 115 when compared to the first assembly 102.

Figure 5A:
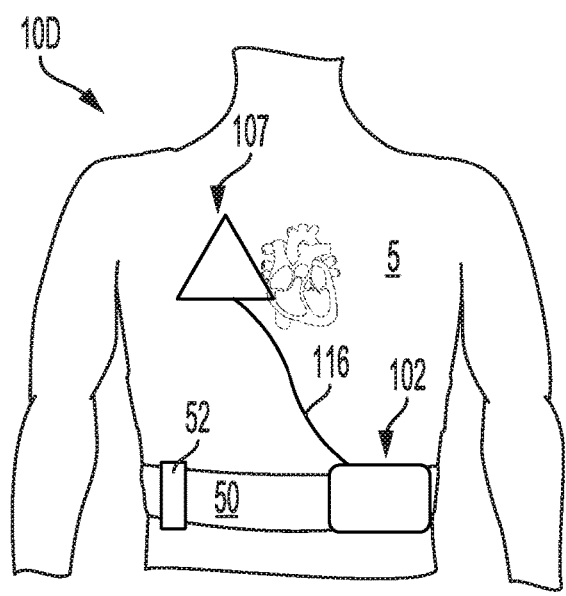
FIG. 5A depicts a schematic of an example wearable cardiac monitoring and treatment device including a wearable support and adhesively coupled portions in wired communication.
Figure 5B:
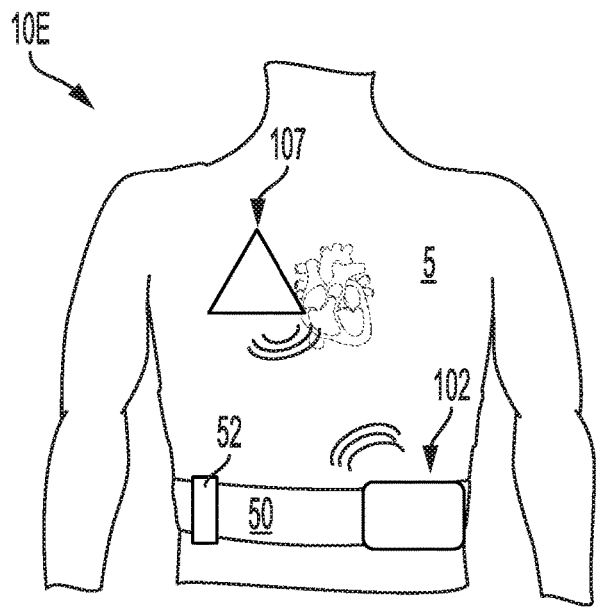
FIG. 5B depicts a schematic of an example wearable cardiac monitoring and treatment device including a wearable support and adhesively coupled portions in wireless communication.
Figure 5C:
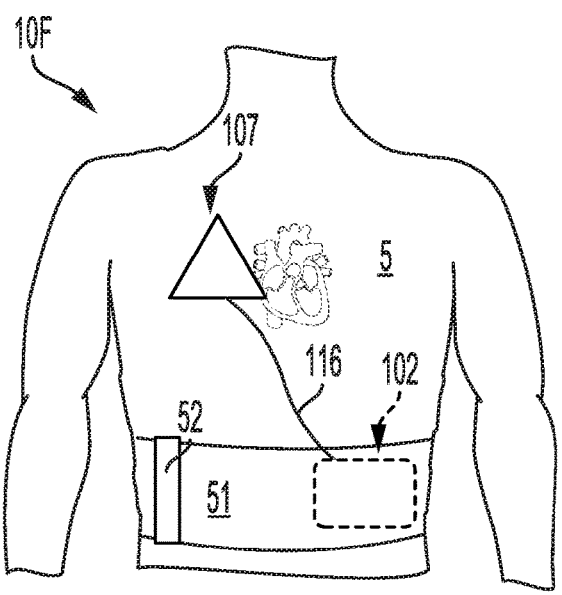
FIG. 5C depicts a schematic of an example wearable cardiac monitoring and treatment device including a wearable support and at least one adhesively coupled portion disposed between the wearable support and a torso of the patient.
Figure 5D:
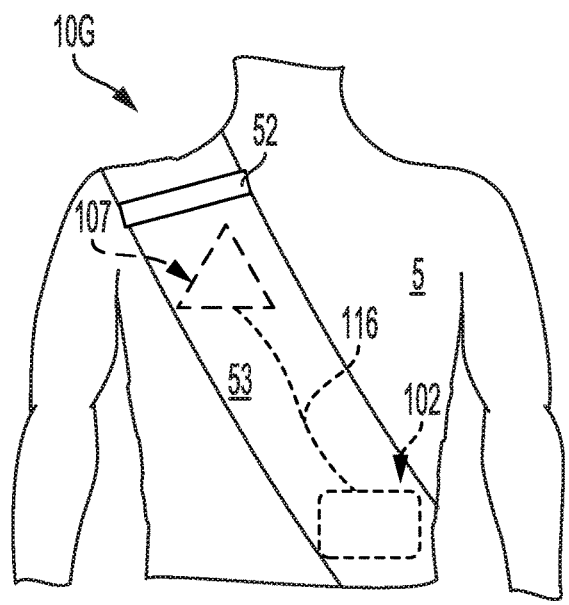
FIG. 5D depicts a schematic of an example wearable cardiac monitoring and treatment device including a wearable support and adhesively coupled portions disposed between the wearable support and a torso of the patient.

In embodiments, such as those of FIGS. 5A-D, the first and second assembly can both be placed on an anterior portion of the torso 5. The second assembly 107 of the device 10D can be placed on the torso 5 above the patient's right nipple, and the first assembly 102 is placed on the left lateral side of the patient's torso 5 opposite placement of the second assembly 107. As shown in FIGS. 5A, 5C, and 5D, in embodiments the device 10D includes a first assembly 102 and second assembly 107 in wired connection. Alternatively, as shown in FIG. 5B, in embodiments the device 10E includes a first assembly 102 and a second assembly 107 in wireless communication, for example when the device is used for monitoring for a cardiac condition. In some examples, the wire 116 can be detachable, and the device 10E can prompt the patient to attach the wire 116 to the first and second assemblies 102, 107 when the device 10E detects a cardiac condition requiring treatment. In implementations at least one of the first assembly 102 and second assembly 107 is on an anterior portion of the torso, and the other is on a posterior portion of the torso. This configuration is useful in establishing an effective treatment vector through the heart for treating the patient with a defibrillation shock, for example.

In the embodiments of FIGS. 5A-B a wearable support can be a belt 50, or waistband, configured for supporting the first assembly 102 and relatively heavier components included therein (e.g., the first assembly weighing around 500 grams-10 kgs). In implementations, the belt 50 can include a tensioner 52 for tightening and/or loosening the belt 50 about the torso 5 of the patient. In implementations, the tensioner 52 can also fasten the belt 50 about the torso 5 of the patient, and can be, for example, a hook and loop fastener system or a ratchet strap and buckle assembly. In embodiments, the first assembly 102 can be disposed on the wearable support or integrated with the wearable support. For example, in FIGS. 5A-B, the first assembly 102 can form a linking portion of the belt 50 so that the sensors integrated with the pad 105 contact the skin of the patient. In some embodiments, the first assembly 102 and/or second assembly 107 can be covered by the wearable support. For example, as indicated by the broken lines in FIGS. 5C-D, the support garment can be a belt 51 positioned on a lower torso region or a sash 53 extending diagonally across the torso 5 and covering the first assembly 102 and/or second assembly 107. In embodiments, the belt 51 and sash 53 can include a tensioner 52 configured for tightening the wearable support about the torso 5, adding compression force to the first assembly 102 and/or second assembly 107 and assisting with maintaining contact of the first and second assemblies 102, 107 with the torso 5.

As described previously, in some examples, the second assembly 107 can include only relatively lighter components such as one or more therapy electrodes 110 and/or one or more ECG sensing electrodes 115. In alternative implementations, the second assembly 107 can include one or more of the heavier components (e.g., the second assembly weighing around 500 grams-10 kgs), such as one or more capacitors, batteries, and/or the therapeutic circuitry when compared to the first assembly 102. Providing additional wearable support, such as a sash 53 as shown in FIG. 5D, for example, can assist with retaining the relatively heavier second assembly 107 that includes heavier components, against an upper region of the torso 5. Providing such additional wearable support assists with preventing the second assembly 107 from pulling on the skin of the patient while adhesively attached.

In examples which will be subsequently described in further detail with regard to FIGS. 6A through 7C, the device 100 can include an adhesively attached first assembly 102 and an adhesively attached second assembly 107 without requiring wearable supports and/or garment-based support. In examples, the system 300 includes the device 100 and a wearable article 400 in wired or wireless communication with the device for transmitting a user input, including an input responsive to an alert for imminent therapy.

The adhesively coupled devices described herein may be configured for short term or long-term use. For example, a patient may be prescribed a short term device for the duration spanning between discharge from a hospital or an out-patient clinical visit and a follow-up medical appointment. In this regard, short-term wear durations may include periods of less than an hour (e.g., 10 minutes to about 60 minutes while in a medical office waiting room), or periods of 1 hour to about 24 hours, 1 hour to about 48 hours, 1 hour to about 72 hours, 1 hour to about 4 days, 1 hour to about a week, and 1 hour to about two weeks. In examples, short-term wear durations may include, for example, durations up to and including around 14 days, or durations up to and including around 30 days.

In another example scenario, a patient may be prescribed a long-term device following a medical appointment to protect the patient from life-threatening arrhythmias, while also collecting diagnostic information for additional, potentially more invasive procedures. In this scenario, such devices can be designed to be used by the patient for an extended period of time that may be greater than the short term duration described above. For example, long-term wear durations can include periods of around 1 month to around 3 months, or around 3 months to around 6 months. Accordingly, advantages of the configurations herein include providing physicians and caregivers with additional diagnostic and therapeutic options for treating patients in their care.

Because these devices require continuous operation and wear by patients to which they are prescribed, advantages of the implementations herein include use of comfortable, non-irritating, biocompatible adhesive and construction materials, and features designed to enhance patient compliance. Such compliance-inducing design features include, for example, device ergonomics, weight of the components and/or distribution of the weight, overall device shape, and inconspicuous appearance when worn under output garments, among others.

The example devices described herein are prescribed to be worn continuously and typically for a prescribed duration of time. For example, the prescribed duration can be a duration for which a patient is instructed by a caregiver to wear the device in compliance with device use instructions. As noted above, the prescribed duration may be for a short period of time until a follow up medical appointment (e.g., 1 hour to about 24 hours, 1 day to about 14 days, or 14 days to about one month), or a longer period of time (e.g., 1 month to about 3 months) during which diagnostics information about the patient is being collected even as the patient is being protected against cardiac arrhythmias. The prescribed use can be uninterrupted until a physician or other caregiver provides a specific prescription to the patient to stop using the wearable medical device. For example, the wearable medical device can be prescribed for use by a patient for a period of at least one week. In an example, the wearable medical device can be prescribed for use by a patient for a period of at least 30 days. In an example, the wearable medical device can be prescribed for use by a patient for a period of at least one month. In an example, the wearable medical device can be prescribed for use by a patient for a period of at least two months. In an example, the wearable medical device can be prescribed for use by a patient for a period of at least three months. In an example, the wearable medical device can be prescribed for use by a patient for a period of at least six months. In an example, the wearable medical device can be prescribed for use by a patient for an extended period of at least one year.

A sudden cardiac arrest or other arrhythmia condition can strike at any time and with little warning. Every patient is encouraged to comply with the device use guidelines, including wearing the device at all times during a prescribed duration, including while showering or sleeping. To improve patient compliance with these guidelines, the devices described herein are lightweight, comfortable, and compact so that they may be concealed under the patient's clothing. Moreover, the devices are configured to allow for uncomplicated application and adherence to the skin of the body of the patient. In some implementations described herein, the devices include various features that promote comfort while continuing to protect the patient from adverse cardiac events. These features can be tailored in accordance with patient comfort preference and can include durable adherence, ease of application and removal, and inconspicuous appearance.

The devices herein are configured to be held against and/or adhesively coupled to a torso of a patient for short term and long-term durations. Adhesively coupled implementations of the device include biocompatible adhesives, such as pressure-sensitive adhesives having tack, adhesion, and cohesion properties suitable for use with a medical device applied to skin for short term and long-term durations. These pressure sensitive adhesives can include polymers such as acrylics, rubbers, silicones, and polyurethanes having a high initial tack for adhering to skin. These pressure sensitive adhesives also maintain adhesion during showering or while a patient is perspiring. The adhesives also enable removal without leaving behind uncomfortable residue. For example, such an adhesive can be a rubber blended with a tackifier.

In addition to biocompatible adhesives, such short term and long-term wear devices include a plurality of sensing electrodes that are disposed on the patient's body and configured to monitor cardiac signals such as electrocardiogram (ECG) signals. The devices, therefore, determine an appropriate treatment for the patient based on the detected cardiac signals and/or other physiological parameters prior to delivering a therapy to the patient. The devices then cause one or more therapeutic shocks, for example, defibrillating and/or pacing shocks, to be delivered to the body of the patient. The wearable medical device includes a plurality of therapy electrodes, and in implementations, at least one of the plurality of therapy electrodes is integrated with a pad as described in detail herein. The plurality of therapy electrodes are disposed on the patient's body and configured to deliver the therapeutic shocks. In some implementations, the devices can also be configured to allow a patient to report his/her symptoms including one or more skipped beat(s), shortness of breath, light headedness, racing heart, fatigue, fainting, and chest discomfort. Device implementations and example features are disclosed herein to improve the ergonomics of such a wearable medical device.

In implementations, the devices include one or more pads configured to be held against and/or adhesively secured to the torso of the patient. One or more energy storage units are operably connected to a therapy delivery circuit. The energy storage units as well as a therapy delivery circuit are housed within at least one housing configured to form a seal with the pad. In implementations, the seal formed is a waterproof seal. In some implementations, a plurality of housings can be disposed on a plurality of segments of the pad. Each of the plurality of housings can include different portions of the device circuitry, such as, ECG acquisition and conditioning circuit(s), therapy delivery circuit(s), energy storage unit(s), processor(s), power source(s) and the like. The energy storage units are configured to store energy for at least one therapeutic pulse (e.g., a defibrillation pulse). The therapy delivery circuit is configured to cause the delivery of the at least one therapeutic pulse via the plurality of therapy electrodes. In implementations, the energy storage units are electrically coupled to the plurality of therapy electrodes (e.g., by a printed circuit board trace, a flex circuit, or a direct contact connection).

As described above, implementations of the wearable medical device 100 described herein are capable of continuous use by patients during either the short term or long-term wear duration. Such continuous use can be substantially continuous or nearly continuous in nature. During substantially continuous or nearly continuous use, the wearable medical device may be continuously used except for sporadic periods during which the use temporarily ceases (e.g., while the patient is refit with a new and/or a different device, while the battery is charged and/or changed, etc.). Such substantially continuous or nearly continuous use as described herein may nonetheless qualify as continuous use. For example, the continuous use can include continuous wear or attachment of the wearable medical device to the patient. In implementations, one or more of the electrodes are continuously attached to the patient as described herein during both periods of monitoring and periods when the device may not be monitoring the patient but is otherwise still worn by or otherwise attached to the patient. Continuous use can include continuously monitoring the patient while the patient is wearing the device for cardiac-related information (e.g., electrocardiogram (ECG) information, including arrhythmia information, cardiac vibrations, etc.) and/or non-cardiac information (e.g., blood oxygen, the patient's temperature, glucose levels, tissue fluid levels, and/or pulmonary vibrations). For example, the wearable medical device can carry out its continuous monitoring and/or recording in periodic or aperiodic time intervals or times (e.g., every few minutes, every few hours, once a day, once a week, or other interval set by a technician or prescribed by a caregiver). Alternatively or additionally, the monitoring and/or recording during intervals or times can be triggered by a user action or another event.

As noted above, the wearable medical device 100 can be configured to monitor other physiologic parameters of the patient in addition to cardiac related parameters. For example, the wearable medical device can be configured to monitor, for example, pulmonary vibrations (e.g., using microphones and/or accelerometers), breath vibrations, sleep related parameters (e.g., snoring, sleep apnea), and tissue fluids (e.g., using radio-frequency transmitters and sensors), among others.

As will be described in detail below, FIGS. 6A-9C depict an example monitoring and treatment device 100 held on a patient's torso 5 only by an adhesive coupling, and FIGS. 1A-B, 3, 4A, 5A-D and 10 relate to adhesively coupled monitoring and treatment devices 10B-C, 10D-G, 100 including one or more wearable supports.

An example arrhythmia monitoring and treatment assembly is shown in FIGS. 6A-7B as an adhesively coupled monitoring and treatment device 100. As shown, the device 100 is external, ambulatory, and adhesively coupled to a patient. The medical device 100 is an external or non-invasive medical device, which, for example, is located external to the body of the patient and configured to provide transcutaneous therapy to the body. The device 100 is an ambulatory medical device, which, for example, is capable of and designed for moving with the patient as the patient goes about his or her daily routine. The device 100 includes a first assembly 102 that includes a pad 105, for example a contoured pad, configured to be adhesively coupled to a torso 5 of a patient. In implementations, a plurality of therapy electrodes and/or a plurality of ECG sensing electrodes can be integrated with the pad 105. Further, as shown in FIGS. 8 and 9A-C the device 100 can include a housing 120 configured to form a watertight seal with the pad 105. In certain implementations, the housing 120 can extend between around 1 cm and 10 cm (e.g., 2 to 9 cm, 3 to 8 cm, 4 to 7 cm) from a surface of the skin 7 of the patient, therefore maintaining a low profile and minimizing any visible protrusion or bulging beneath clothing. In implementations, this height includes the thickness of the pad 105. To achieve this low profile configuration, a housing 120 of the assembly 102 includes compact components thereunder that are organized in a compact assemblage as will be described subsequently with regard to implementations. In some examples, the compact components are nested and arranged so that the housing 120 has an asymmetrical vertical profile that is narrower on an upper end than on a lower end, and heavier components are aggregated in the relatively more volumetric lower end of the housing for patient comfort. For example, the housing 120 can include at least an ECG acquisition and conditioning circuit 125, a therapy delivery circuit 130, and a processor 118. For example, the processor 118 can analyze the ECG signal of the patient received and conditioned via the ECG acquisition and conditioning circuit 125 and detect one or more treatable arrhythmias. The processor 118 can cause the therapy delivery circuit 130 to deliver at least one defibrillation pulse to the patient on detecting the one or more treatable arrhythmias. As described in further detail below, the device 100 includes components with particular physical dimensions, weights, and functional properties that in combination cause the overall weight of the device 100 to be in a range of 250 grams to 2,500 grams while enabling the device 100 to function as a monitoring and treatment device.

In examples, the first assembly 102 can be coupled to a second assembly 107 that includes a second, different pad 109 as shown in FIGS. 6A-7B, and as will be subsequently described in further detail. For example, the second assembly 107 can be configured to be located at an upper right anterior position of the patient's torso 5 as shown in FIGS.

Figure 6A:
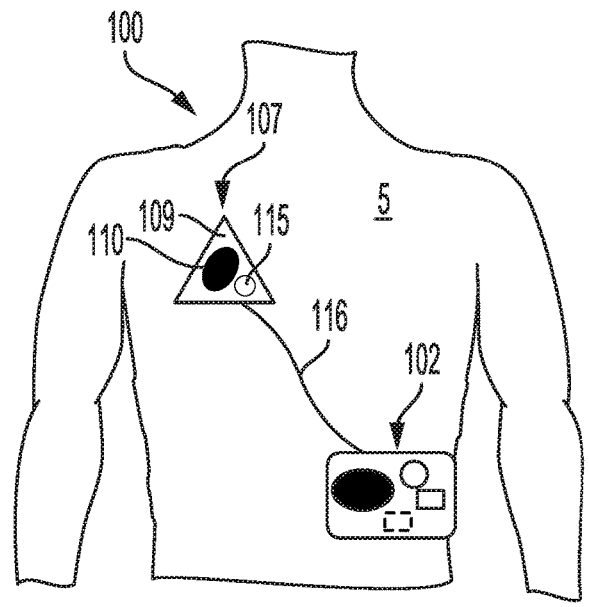
FIG. 6A depicts a schematic of an example adhesively coupled wearable cardiac monitoring and treatment device including anterior mounted first and second assemblies.
Figure 6B:
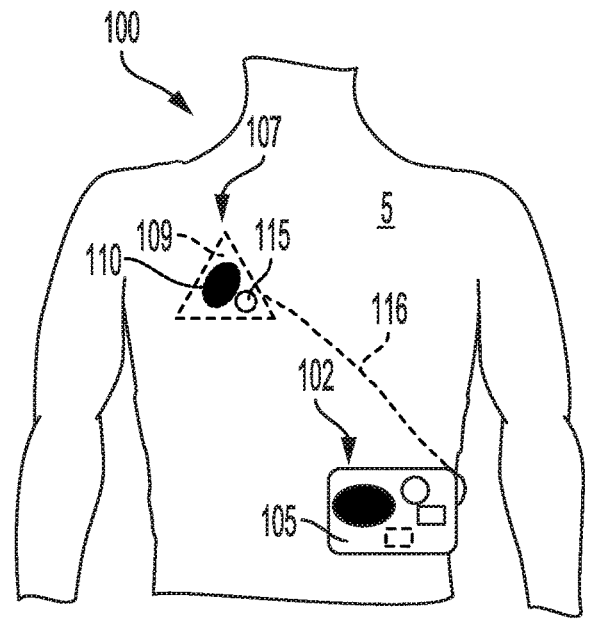
FIG. 6B depicts a schematic of an example adhesively coupled wearable cardiac monitoring and treatment device including a posterior mounted first assembly and an anterior mounted second assembly.
Figure 6C:
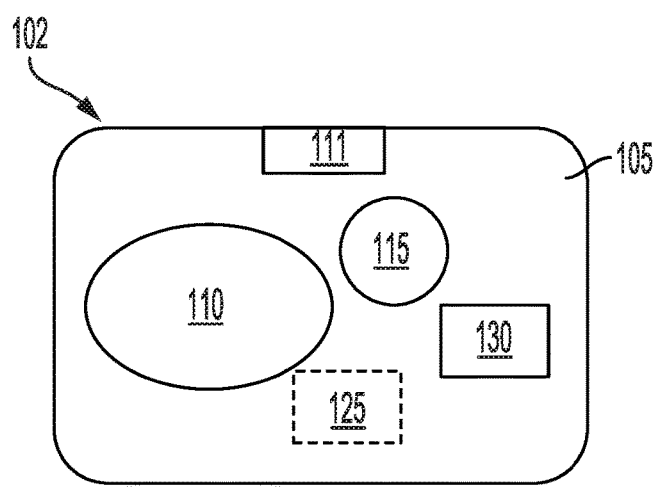
FIG. 6C depicts a schematic of an example of a portion of the adhesively coupled wearable cardiac monitoring and treatment device of FIGS. 6A and 6B.

6-7B. In other examples, the second assembly 107 can be configured to be located at an upper posterior position of the patient's torso 5, such as the upper right posterior position, as shown in FIG. 6B. In implementations at least one of the first assembly 102 and second assembly 107 is on an anterior portion of the torso 5 and the other is on a posterior portion of the torso 5. This configuration is useful in establishing an effective treatment vector through the heart for treating the patient with a defibrillation shock, for example. Although the implementations of FIGS. 6A-7B depict a substantially rectangular shaped first assembly 102 and a triangle shaped second assembly 107, the shapes of the first and second assemblies can be any shape including, for example, a polygon, a square, a circle, an oval, an octagon, a trefoil, a trapezoid, a polygon, or a non-polygon shape custom-tailored to a patient's contours and/or preferences. In implementations, the second assembly 107 can include one or more of the components and/or materials described with regard to implementations of the first assembly 102, such as the components and materials described with regard to the implementations of FIGS. 8-9.

The pad 105 is configured to be adhesively coupled to a torso 5 of a patient. The pad 105 is formed from a flexible material and is configured to conform to a unique curvature of a region of the torso 5 of the patient. Additionally or alternatively, as shown schematically in FIG. 3C, the pad 105 can include a plurality of segments separated by a flexible material to conform the pad 105 to the curvature of a region of the torso 5 to which it is applied. The pad 105 can be configured to conform with a curvature of a portion of the patient's torso 5, such as lower portion of the torso, an upper anterior portion of the torso, upper posterior portion of the torso, or one or more lateral portions of the torso. In implementations including a pad 105 formed from a conforming material and/or segments, the pad could accommodate various body shapes and sizes and also shape changes associated with movement of the patient's body. For example, the pad 105 could accommodate stretching, expansion, and contraction of a lower region of the torso 5 while a patient stands, walks, sits, or lies down.

In implementations, the pad 105 can be sized to accommodate various body sizes. In some implementations, the pad 105 can be manufactured in various sizes accommodating a range of body sizes. The particular shape and size of the pad 105 can be pre-configured or uniquely customized for the patient. For example, various body size measurements and/or contoured mappings may be obtained from the patient, and a uniquely tailored contoured pad 105 may be 3D printed from, for example, any suitable thermoplastic (e.g., ABS plastic) or any elastomeric and/or flexible 3D printable material. The pad 105 therefore accommodates variable patient sizes and/or contours, and/or some or all portions of the pad can be customized to fit to a patient's particular body size and contour.

In examples, the patient may apply the pad 105 in a uniquely preferred orientation and location. Enabling a patient, in consultation with their caregiver, to place the device 100 in a comfortable location and orientation encourages patient compliance with continuous wear throughout the prescribed duration of wear. For example, the pad 105 can be positioned by a caregiver or physician on the torso of the patient in a first location at the start of the prescribed duration of wear. At least one of the patient, caregiver, and physician may relocate the pad 105 to a second location overlapping with, tangential to, adjacent to, or apart from the first location but within a prescribed region of the torso. For example, the first assembly 102 can be placed initially on a lower anterior region of the torso, along the line of the bottom of a patient's rib cage for comfort and to minimize the appearance of any bulges in clothing worn over the device 100. A patient, caregiver, or physician may remove and re-adhere the pad 105 at a new location distanced from the previous location by one inch, for example, in any lateral and/or rotational direction. This provides the patient's skin with an opportunity to breath and regenerate (e.g., slough) and reduces the effects of skin irritation that may be caused by adhesives. By keeping the pad in the region of initial application, the first assembly 102 of the device 100 continues to function in conjunction with the second assembly 107, which is positioned relative to the first assembly and with particular attention to the shock vector traveling between the assemblies 102, 107 and through the heart.

In embodiments, the pad 105 is designed to be durable, flexible, and breathable so as to allow perspiration to evaporate. In embodiments, the pad 105 is non-irritating when contacting skin as described above with regard to skin irritation grading as set forth in Table C.1 of Annex C of American National Standard ANSI/AAMI/ISO 10993-10: 2010. In examples, the pad 105 is generally non-conductive, flexible, water vapor-permeable, and substantially liquid-impermeable or waterproof. The non-conductive flexible, water-vapor permeable pad 105 may comprise or consist of polyurethane, such as TEGADERM polyurethane film (available from 3M), OPSITE polyurethane film (available from Smith & Nephew, London, United Kingdom), or HYDROFILM polyurethane film (available from Hartman USA, Rock Hill, S.C.). In other examples, the pad 105 can comprise or consist of at least one of neoprene, thermo-formed plastic, or injection molded rubber or plastic, such as silicone or other biocompatible synthetic rubber. In examples, the pad 105 is a laminated pad including a waterproof or water resistant layer applied to a relatively more rigid plastic or rubber layer configured to provide structural support for a housing and electronic components disposed therein. In examples the pad 105 is perforated to aid in moisture evaporation from the skin.

Figure 8:
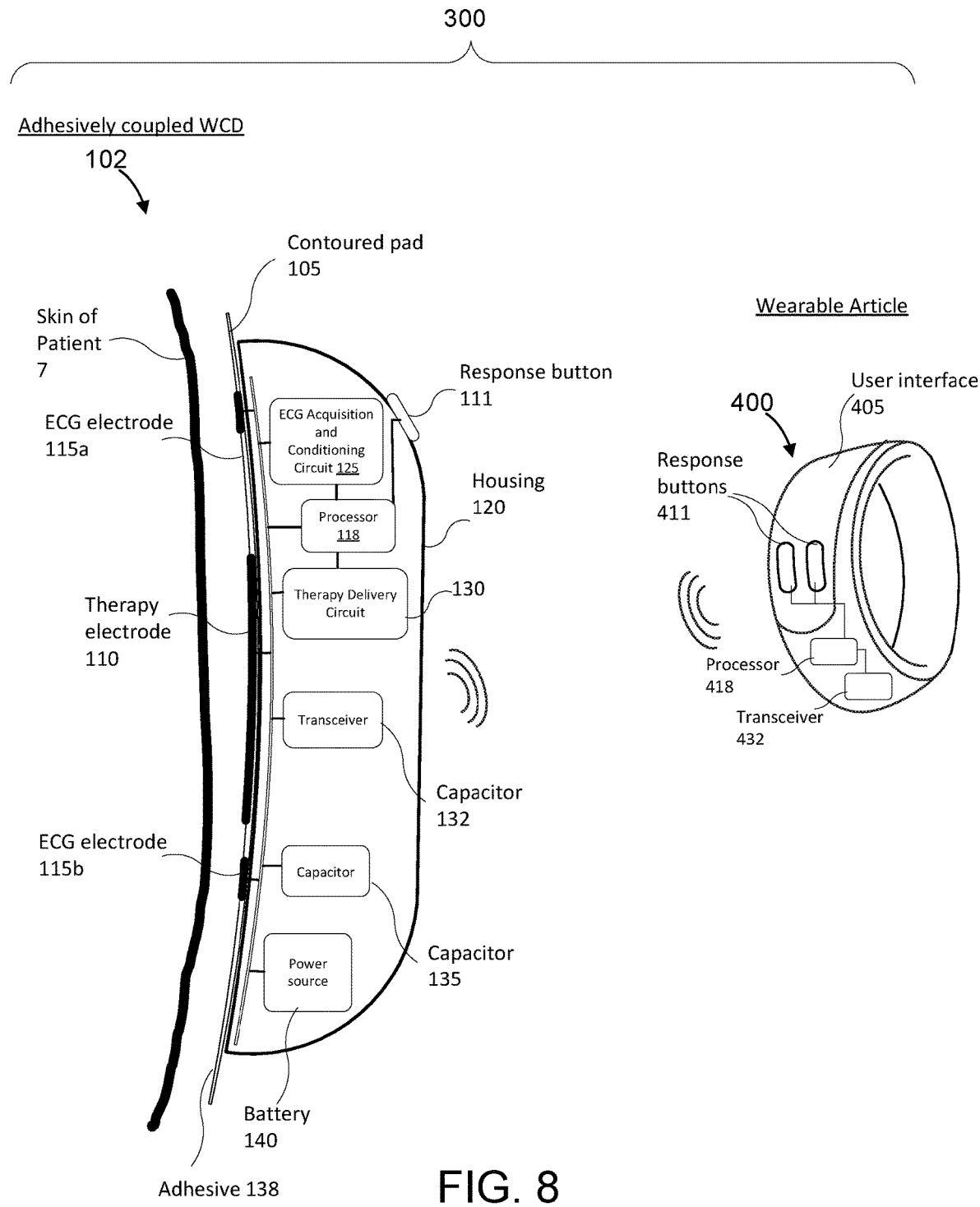
FIG. 8 depicts a side cross-section schematic of an example wearable cardiac monitoring and treatment device in communication with a wearable article.

In embodiments, the device 100 can include a conductive adhesive layer 138, as indicated in FIG. 8. As described in U.S. Pat. No. 9,867,976, titled "LONG-TERM WEAR ELECTRODE," issued on Jan. 16, 2018 (hereinafter the "'976 patent"), which is hereby incorporated herein by reference in its entirety, a water-vapor permeable conductive adhesive material can be, for example, the flexible, water vapor-permeable, conductive adhesive material comprising a material selected from the group consisting of an electro-spun polyurethane adhesive, a polymerized microemulsion pressure sensitive adhesive, an organic conductive polymer, an organic semi-conductive conductive polymer, an organic conductive compound and a semi-conductive conductive compound, and combinations thereof. In an example, a thickness of the flexible, water vapor-permeable, conductive adhesive material can be between 0.25 and 100 mils. In another example, the water vapor-permeable, conductive adhesive material can comprise conductive particles. In implementations, the conductive particles may be microscopic or nano-scale particles or fibers of materials, including but not limited to, one or more of carbon black, silver, nickel, graphene, graphite, carbon nanotubes, and/or other conductive biocompatible metals such as aluminum, copper, gold, and/or platinum.

FIG. 8 depicts the first assembly 102, which is a portion of the device 100. The device 100 includes a pad 105 and a housing 120 configured to form a watertight seal with the pad 105. Referring now to FIG. 8, the assembly 102 includes at least one of a plurality of therapy electrodes 110 integrated with the pad 105. Example therapy electrodes 110 include, for example, conductive metal electrodes, such as those made of stainless steel, tin or aluminum, a conductive ink, or a conductive polymer. The assembly 102 can also include at least one of a plurality of ECG sensors 115 integrated with the pad 105. In the implementation of FIG. 6, two ECG sensors 115a and 115b are shown to be integrated with the pad 105. In examples, the ECG sensors 115 monitor a patient's ECG information. As described in detail in subsequent examples, the ECG sensors 115 can be non-polarizable ECG electrodes (e.g., clinical grade Ag/AgCl electrodes) or polarizable electrodes (e.g., electrodes having a metal substrate with an oxide layer, such as a $Ta_2O_5$ coating) configured to measure changes in a patient's electrophysiology to measure the patient's ECG information. Example ECG sensors 115 include tantalum pentoxide electrodes, as described in, for example, U.S. Pat. No. 6,253,099 entitled "Cardiac Monitoring Electrode Apparatus and Method," the content of which is incorporated herein by reference. In implementations, the ECG sensors 115 may be made of a core plastic or metal substrate element that is coated with a thick-film polymeric compound filled with a conductive Ag/Ag/Cl metallic filler.

In some examples, as indicated FIG. 8, at least one therapy electrode 110 and one or more ECG sensors 115 are formed within the pad 105 such that a skin contact surface of each component is coplanar with or protrudes from the patient contact face of the pad 105. In examples, the therapy electrode 110 and the ECG sensors 115 are disposed on the patient contact face of the pad 105. In some implementations, the therapy electrode 114 and ECG sensors 115 are metallic plates (e.g. stainless steel) or substrates that are formed as permanent portions of the device 100. A metallic plate or substrate can be adhered to the pad 105, for example, by a polyurethane adhesive or a polymer dispersion adhesive such as a polyvinyl acetate (PVAc) based adhesive, or other such adhesive. In examples, the plurality of ECG sensors 115 are a plurality of dry ECG sensing electrodes. In examples, the ECG sensors 115 are flexible, dry surface electrodes such as, for example, conductive polymer-coated nano-particle loaded polysiloxane electrodes mounted to the pad 105. In some examples, the ECG sensors 115 are flexible, dry surface electrodes such as, for example silver coated conductive polymer foam soft electrodes mounted to the pad 105. In examples, the ECG sensors 115 are screen printed onto the pad 105 with a metallic ink, such as a silver-based ink. In implementations, each of the therapy electrodes 110 has a conductive surface adapted for placement adjacent the patient's skin. In some implementations, the therapy electrodes 110 can include an impedance reducing material and/or mechanism as subsequently described.

In implementations, the at least one therapy electrode 110 and at least one ECG sensor 115 are manufactured as integral components of the pad 105. For example, the therapy electrode 110 and/or the ECG sensor 115 can be formed of the warp and weft of a fabric forming at least a layer of the pad 105. In implementations, the therapy electrode 110 and the ECG sensors 115 are formed from conductive fibers that are interwoven with non-conductive fibers of the fabric.

The assembly 102 includes an ECG acquisition and conditioning circuit 125 disposed within the at least one housing 120 and electrically coupled to the plurality of ECG sensors 115 to provide at least one ECG signal of the patient. In examples, the ECG acquisition and conditioning circuit 125 includes a signal processor configured to amplify, filter, and digitize the cardiac signals prior to transmitting the cardiac signals to a processor 118 of the device 100. The ECG sensors 115, therefore, can transmit information descriptive of the ECG signals to a sensor interface via the ECG acquisition and conditioning circuit 125 for subsequent analysis.

In examples, as shown in FIG. 8, a therapy delivery circuit 130 is disposed within the at least one housing 120 and configured to deliver one or more therapeutic pulses to the patient through the plurality of therapy electrodes 110 of the device 100. In examples, the processor 118 is disposed within the at least one housing 120 and is coupled to the therapy delivery circuit 130. The processor 118 is configured to analyze the ECG signal of the patient and detect one or more treatable arrhythmias based on the at least one ECG signal. The processor 118 is configured to cause the therapy delivery circuit 130 to deliver at least one defibrillation pulse to the patient on detecting the one or more treatable arrhythmias.

As shown in FIGS. 8 and 9, in examples, one or more printed circuit boards 145 connect various circuitry and hardware components (e.g., processor 118, therapy delivery circuit 130, therapy electrodes 110, ECG acquisition and conditioning circuit 125, ECG sensing electrodes 115, etc.) of the first assembly 102. The printed circuit board 145 can route signals between the therapy delivery circuit 130 and the therapy electrodes 110 and the ECG acquisition and conditioning circuit 125 and the ECG sensing electrodes 115. In implementations of the pad 105 comprising a plurality of segments separated by a flexible material, the one or more circuit boards 145 can be apportioned among some or all of the plurality of segments and, in examples, maybe be electrically interconnected by one or more wires and/or flexible traces or cables.

Continuing with the description of the implementations of the device 100 of FIGS. 7A-9C, in implementations, the therapy delivery circuit 130 is operatively connected to one or more capacitors 135. In implementations, the one or more capacitors provide a total capacitance of 162 µF. In implementations the one or more capacitors 135 is a plurality of capacitors (e.g., three, four or more capacitors) that can be switched into a series connection during discharge for a defibrillation pulse. For example, four capacitors of approximately 650 µF can be used. In one implementation, the capacitors can have between 200 to 2500 volt surge rating and can be charged in approximately 5 to 30 seconds from a battery 140 depending on the amount of energy to be delivered to the patient. Additional implementations of capacitor properties and arrangement within the device 100 are provided herein in subsequent sections.

For example, each defibrillation pulse can deliver between 60 to 400 joules (J) of energy. In some implementations, the defibrillating pulse can be a biphasic truncated exponential waveform, whereby the signal can switch between a positive and a negative portion (e.g., charge directions). An amplitude and a width of the two phases of the energy waveform can be automatically adjusted to deliver a predetermined energy amount.

In implementations, the therapy delivery circuit 130 includes, or is operably connected to, circuitry components that are configured to generate and provide the therapeutic shock. As will be described in detail subsequently with regard to implementations of the device 100, the circuitry components include, for example, resistors, one or more capacitors 135, relays and/or switches, an electrical bridge such as an H-bridge (e.g., an H-bridge circuit including a plurality of switches, (e.g. insulated gate bipolar transistors or IGBTs, silicon carbide field effect transistors (SiC FETs), metal-oxide semiconductor field effect transistors (MOSFETS), silicon-controlled rectifiers (SCRs), or other high current switching devices)), voltage and/or current measuring components, and other similar circuitry components arranged and connected such that the circuitry components work in concert with the therapy delivery circuit 130 and under control of one or more processors (e.g., processor 118) to provide, for example, one or more pacing or defibrillation therapeutic pulses.

Referring now to FIG. 8, the system 300 as disclosed herein includes an adhesively coupled assembly 102 as previously described, and the adhesively coupled assembly is in communication with a wearable article 400. The wearable article is configured to be disposed on a readily accessible location on the patient's body and to be worn simultaneously with the device 100. As previously described with regard to FIGS. 1A-B the wearable medical device 100 is configured to be worn on the torso 5 of the patient and discreetly extend from the skin surface of the patient under clothing worn over the device 100.

As shown in FIG. 8, a housing 120 of the assembly 102 can extend between around 1 cm and 10 cm from a surface of the skin of the patient, therefore maintaining a low profile and minimizing any visible protrusion or bulging beneath clothing. In implementations, the housing 120 can extend between around 0-5 cm from the skin surface of the patient. In implementations, the housing 120 can extend between around 5-10 cm from the skin surface of the patient. In implementations, the housing 120 can extend between around 2-9 cm from the skin surface of the patient. In implementations, the housing 120 can extend between around 3-8 cm from the skin surface of the patient. In implementations, the housing 120 can extend between around 4-7 cm from the skin surface of the patient. In implementations, the height of the housing 120 from the skin surface includes the thickness of the pad 105, which can range from about 0.1 cm to 2 cm. The housing 120 can include at least an ECG acquisition and conditioning circuit, a therapy delivery circuit, and a processor. For example, the processor can analyze the ECG signal of the patient received and conditioned via the ECG acquisition and conditioning circuit and detect one or more treatable arrhythmias. The processor can cause the therapy delivery circuit to deliver at least one defibrillation pulse to the patient on detecting the one or more treatable arrhythmias.

In implementations, the housing 120 can include a surface coating to lower a friction value and/or a static cling value between the housing 120 and an article of clothing worn over the housing 120. For example, the housing 120 may be treated with a silicone spray and/or a Teflon coating to allow clothing to slide past the housing 120 rather than adhere to or snag on the housing 120. Preventing or lowering adhesive forces between the housing 120 and an article of clothing assists with minimizing visibility of the device 100 to onlookers and encouraging patient compliance with wearing the assembly 102 throughout a prescribed duration. In an embodiment, the outer surface of the housing 120 may be made of an electrostatically dissipative material such as a conductor-filled or conductive plastic in order to prevent static cling of a patient's clothing. Alternatively, in embodiments, the housing 120 is made of a non-conductive plastic coated with a static dissipative coating such as LICRON CRYSTAL ESD Safe Coating (TECHSPRAY, Kennesaw, Ga.), a clear electrostatic dissipative urethane coating.

Figure 9A:
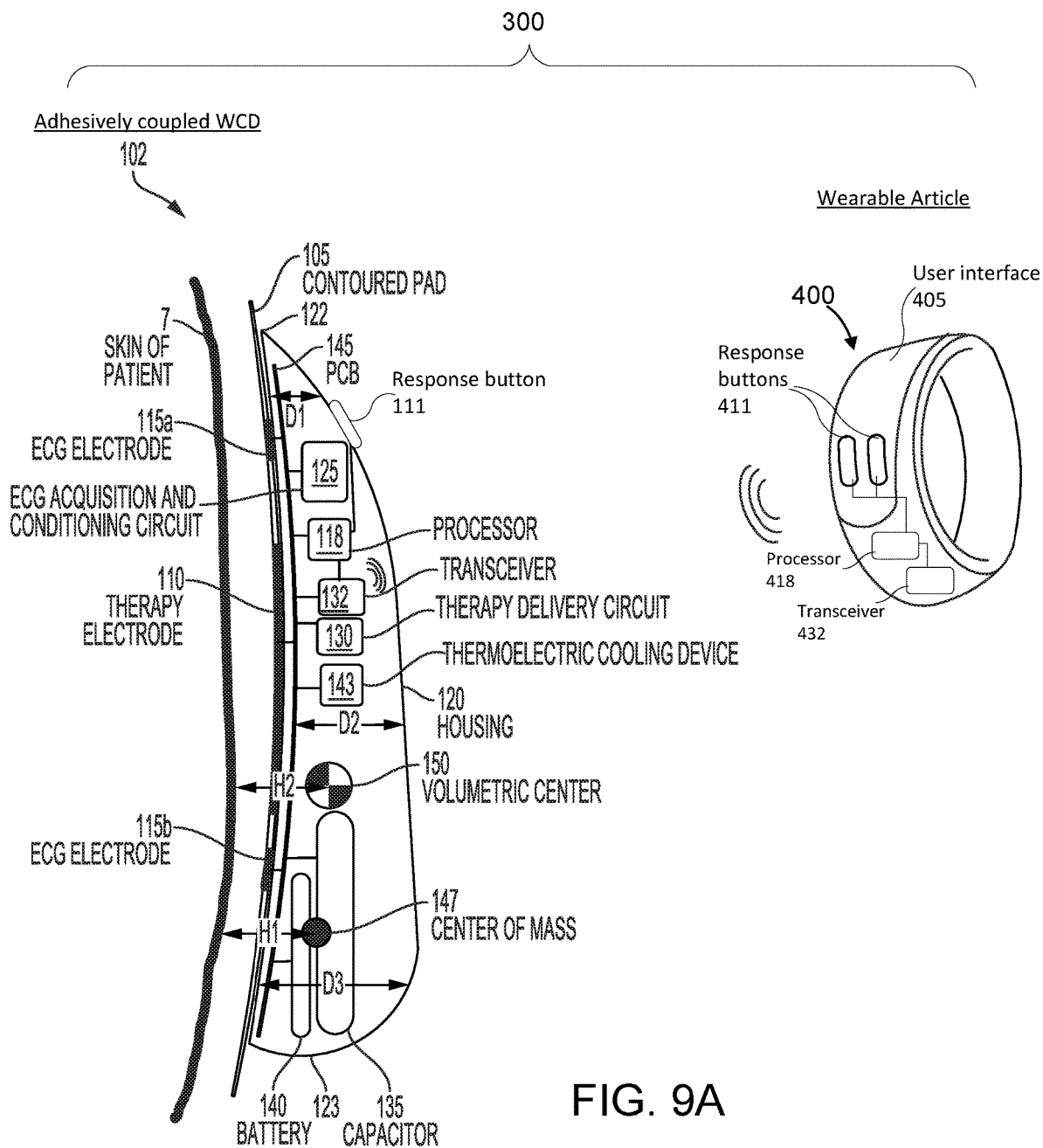
FIG. 9A depicts a side cross-section schematic of an example ergonomic wearable cardiac monitoring and treatment device in communication with a wearable article.

Additionally or alternatively, in examples, such as that of FIGS. 9A-B, the first assembly 102 of the device 100 has an ergonomic profile as will now be described. For example, the housing 120 extends a distance D of between around 1 cm and 5 cm from a surface of a pad 105. In the example of FIG. 9A, in which the center of mass 147 is below the volumetric center 150 and the heavier and/or larger components are below the volumetric center 150, the housing 120 can be shaped to follow the general contour of the components housed therein. For example, the distance D at which the housing 120 extends from the surface of the pad 105 can vary from a top end 122 to a bottom end 123 (e.g., while the first assembly 102 is worn such that the top end is oriented closer to a head of the patient than the bottom end). In one example, the side profile has the appearance of a right triangle with rounded surfaces and edges, or an approximately teardrop shape. In the example of FIGS. 9A-B, the distance D1 at the top end 122 of the first assembly 102 is shorter than the distance D2 at the middle, and the distance D2 at the middle is shorter than the distance D3 at the bottom end 123. The example profile of the housing 120 of FIGS. 9A-9B provides a comfortable weight distribution that reduces pulling on the skin under gravitational forces attempting to rotate the top end 122 away from the torso 5. The teardrop shaped cross-section of the first assembly, therefore, offsets the peel force tending to pull the pad 105 away from the torso. Additionally, the streamlined profile shape follows the contours of a lower anterior region of the torso 5 compactly such that the device 100 is unnoticeable or protrudes very little when worn beneath a garment of clothing. Such a comfortable, compact configuration encourages patient compliance by maintaining a patient's privacy during the prescribed duration of wear.

Figure 9C:
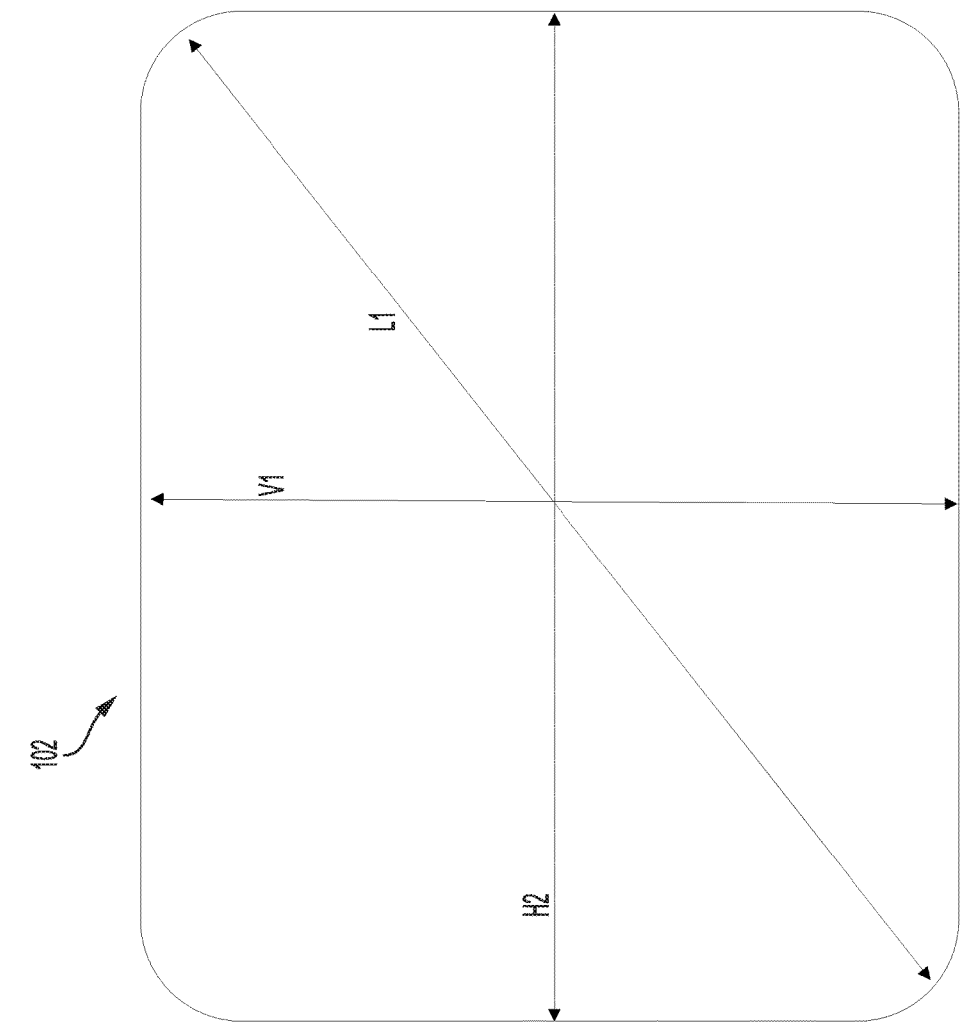
FIG. 9C depicts a dimensioned front plan view of the example ergonomic wearable cardiac monitoring and treatment device of FIGS. 9A and 9B.
Figure 9B:
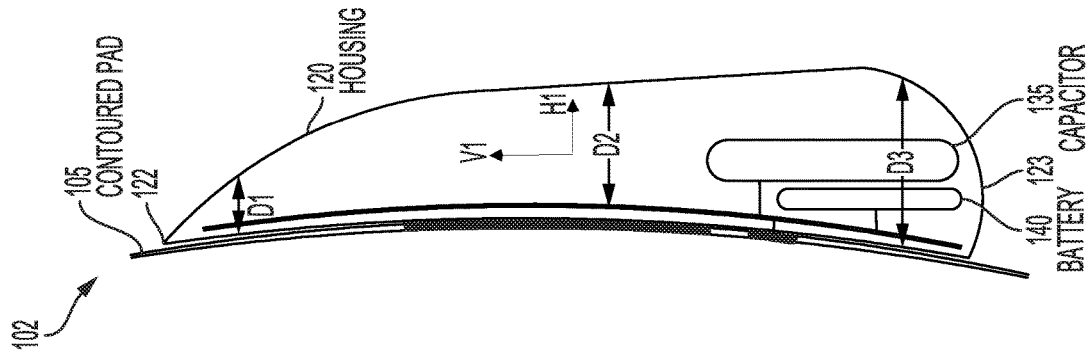
FIG. 9B depicts a dimensioned asymmetrical vertical side profile schematic of the example ergonomic wearable cardiac monitoring and treatment device of FIG. 9A.

As shown in the simplified view of FIGS. 9B-C, in implementations, a vertical side profile of the arrhythmia monitoring and treatment assembly 102 is asymmetrical about one or both of a horizontal axis H1, H2 and a vertical axis V1. For example, a tallest height, e.g., distance D3, of the arrhythmia monitoring and treatment assembly from the skin surface is disposed lower on the torso than a shortest height e.g., distance D1, of arrhythmia monitoring and treatment assembly. In implementations, a ratio of the tallest height to the shortest height is in a range from 10:1 to 2:1. In implementations, such as that shown in FIG. 9A, the asymmetrical housing 120 has a greater volume on a lower end 123. At least one of one or more batteries 140 and one or more capacitors 135 are disposed within a portion of the housing 120 having the tallest height, e.g., D3 located toward the lower end 123. As described subsequently with regard to implementations of compact batteries, the one or more batteries 140 can have a combined envelope volume of one quarter or less than the volume bounded by the housing 120 of the arrhythmia monitoring and treatment assembly and the pad 105 and/or skin surface 7 of the patient. As described subsequently with regard to implementations of compact batteries the one or more batteries can have a capacity in a range of 200-8000 mAh.

As described previously, in implementations, the housing 120 extends a distance D of between around 1 cm and 10 cm from a surface of the pad and/or the skin of the patient on which the assembly 102 is disposed. For example, the housing 120 can extend 1 cm, 1.5 cm, 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, 9.5 cm and 10 cm from the pad 105 and/or the skin 7 of the patient on which the assembly 102 is disposed. In addition to maintaining a center of mass 147 below the volumetric center 150, the assembly 102 maintains a low profile and is inconspicuously worn under a patient's clothing. The housing 120 does not protrude so far from the skin 7 of the patient so as to cause one or more noticeable bulges beneath clothing and therefore more seamlessly integrates with a patient's lifestyle. Patients who feel less disrupted by wearing the system 300 are more likely to comply with wearing the system 300 for the prescribed duration. In examples, the volume under the housing 120, and therefore the distance of the housing from the surface of the pad, depends upon a combination of component sizes, shapes, and relatively placements. In implementations, patient comfort and compliance is encouraged further by establishing comfortable sizing of the device. For example, as shown in FIGS. 9B-C taken together, a longest axis L1 of the arrhythmia monitoring and treatment assembly is in a range of between 2 to 20 times longer than a tallest height, e.g. D3, of the housing 120 from the skin surface. In implementations, the height of the housing 120 from the skin surface includes the thickness of the pad 105, which can range from about 0.1 cm to 2 cm. A flatter, wider device 100 having a flexible interface layer for attaching to the skin of the patient enables a more comfortable weight distribution about the torso 5 of the patient while minimizing any protrusions that might be perceived by onlookers. By increasing the discreet nature of the housing 120 and the overall system 300 and minimizing any potential discernment by onlookers, patients will feel more confident in maintained privacy throughout the duration of prescribed wear.

As previously described, the device 100 is configured for providing therapy to the patient on detecting one or more arrhythmia conditions of the patient. In implementations, both the device 100, including the assembly 102, and the readily accessible wearable article 400 include patient input features for communicating with and providing controlling input to the system 300. Such communications can include, for example, a patient input that delays or prevents delivery of a treatment by the device 100, such as a defibrillation or pacing shock. As described previously with regard to the implementation of FIG. 8, the system 300 of FIG. 9A includes a wearable article 400 in communication with the assembly 102. A first at least one user response button 111 is disposed on the housing 120 of the assembly 102 concealed under clothing. In implementations, the first at least one user response button 111 includes two or more buttons disposed on the housing 120, and the processor 118 requires input to both of the two or more buttons simultaneously to delay delivery of a treatment. In implementations, as shown in FIGS. 8 and 9A, the first at least one user response button 111 is at least one tactile response button disposed on the housing 120, and the at least one tactile response button 111 is raised or depressed relative to a housing surface so as to be palpable beneath the one or more layers of clothing.

Because the assembly 102 is configured to be concealed under clothing of the patient the first one or more user response buttons 111 are not readily accessible while concealed. The patient either actuates the first at least one user response button 111 by blindly pressing atop one or more layers of clothing to locate and actuate the first one or more user response buttons 111 or by lifting or removing the one or more layers of clothing to expose the first at least one user response buttons 111 and some or all of the patient's torso 5. Both options require time and dexterity, and the latter lacks patient privacy. The patient, therefore, may benefit from a more readily accessible input for communicating with the assembly 102.

The second at least one user response button 411 is configured to be worn on a second location of the patient's body at a location other than the torso 5 such that the second at least one user response button 411 is readily accessible to the patient. In the example of FIGS. 1A-B, the wearable article 400 is a wrist worn device disposed on the body of the patient at or near a sleeve opening 505 of a shirt 500 worn over the low-profile device 100. Such wrist worn articles 400 can resemble and/or also function as commonly worn devices such as a watch, a bracelet, or fitness device, adding to the discretion of the system 300. The privacy, ease of use, and modesty provided by a wrist worn article encourages patient compliance with simultaneously wearing the wearable article 400 with the assembly 102. As shown in FIG. 9A, the second at least one user response button 411 comprises at least one of a mechanically-actuatable button, a touch screen interface, and at least one touch screen button on a user interface 405 of the wearable article 400.

As described previously, in implementations, a processor 118 disposed in the assembly 102 is configured to analyze an ECG signal of the patient received via the assembly 102 to detect one or more arrhythmia conditions of the patient. In response to detecting one or more arrhythmia conditions, the processor 118 is configured to cause the system 300 to provide a warning of an impending therapy to be delivered to the patient. Responsive to the warning of an impending therapy, the patient may then suspend the impending therapy by inputting a command to the processor 118 by touching and/or pressing at least one of the first at least one user response button 111 and the second at least one user response button 411. Because the assembly 102 is configured to be worn under clothing, such as a shirt 500, the second at least one user response button 411 provides the patient with a readily accessible interface for communicating with the processor 118 at the sounding of an impending treatment alarm.

In implementations, an accessible wearable article 400 is disposed on the body of the patient at a location other than the torso 5 for easy reach and/or retrieval. Such a location, for example, may include a position about the waist of the patient, on a wrist, arm, or hand of the patient, or at, near, or about the neck of the patient. In implementations of the system 300, the wearable article 400 comprises at least one of a bracelet, a ring, a retractable pendant, a necklace, a belt configured to be worn over the clothing, a sash configured to be worn over the clothing, a bolo tie, a watch, an arm band, a bracelet, and a patch configured to be worn over the clothing of the patient at an accessible location not entrapped by clothing. In implementations, the accessible wearable article 400 is readily accessible such that it is not concealed under clothing. In implementations, the readily accessible wearable article is located on an uncovered area of the patient's body or is at least partially disposed under the clothing of the patient near an opening in a garment. For example, the wearable article may be disposed on a patch or lanyard located adjacent a shirt neckline, just under a shirt neck hole for quick and easy reach.

Figure 10:
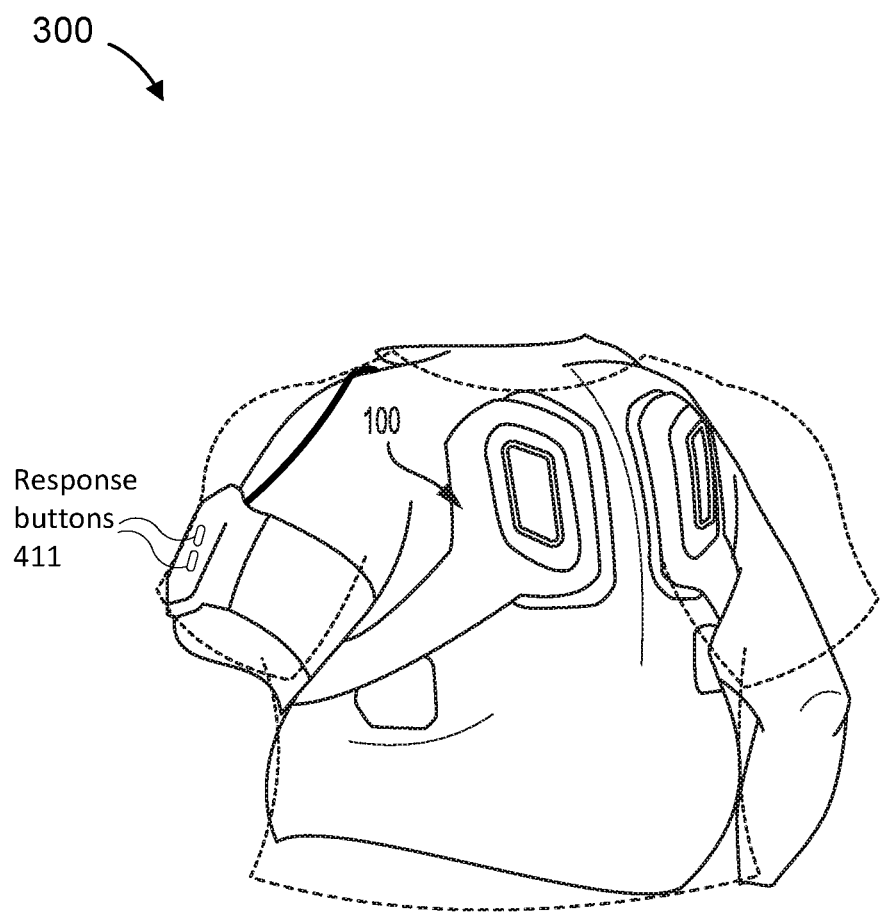
FIG. 10 depicts a rear perspective view of an example of an adhesively coupled wearable cardiac monitoring and treatment device including a wearable support and a wearable article in communication with the device.

In implementations, such as that of FIG. 10 the wearable article 400 comprises adjustable arm band configured to be worn along the length of an arm of the patient. For example the arm band may be an elastomeric band configured to be worn on an upper arm when the patient wears a short sleeve shirt and then slid to a wrist position when the patient wears a long sleeve shirt. Such an arm band may include a hook and loop fastening system or other adjustable closure mechanism for tightening the wearable article 400 around a variable circumference of a patient's arm.

In implementations, the second at least one user response button 411 is disposed on a handheld device operated by the patient. For example, the handheld device may include a smart phone device, tablet, or dedicated handheld unit paired with the arrhythmia monitoring and treating assembly (e.g., the wearable medical device 100) of the system 300 and in wireless communication with a processor 118 of the assembly 102.

In implementations, the device 100 communicates with the wearable article 400 via wired and/or wireless communication links. In examples, as shown in FIGS. 8 and 9, the device 100 includes a receiver and/or transceiver 132 in communication with the processor 118 and configured to communicate with the wearable article 400. The wearable article 400 includes a transceiver 432 for receiving communications from the device 100 and communicating user inputs from the second at least one user response button 411 to the processor 118 of the assembly 102.

In implementations, the processor 118 and wearable article 400 are in wireless communication, either directly or indirectly via a network. Such communication links can include BLUETOOTH, broadband cellular technology (e.g., 2.5G, 2.75G, 3G, 4G, 5G cellular standards), and/or Long-Term Evolution (LTE) technology or GSM/EDGE and UMTS/HSPA technologies for high-speed wireless communication. In some implementations, the device 100 and wearable article 400 may communicate with a remote server over a WI-FI communications link based on the IEEE 802.11 standard. In some implementation, the device 100 and wearable article may communicate over a body area network based on the IEEE 802.15 standard.

In implementations, the second at least one user response button 411 is uniquely paired with the arrhythmia monitoring and treatment assembly 102. In implementations, a wearable article 400 further comprises one or more sensors configured to verify an identity of the patient based on at least one of audible, touch-based, signal-based, and visible information, and delay therapy delivery based at least in part on the verified identity. In implementations, at least one of the arrhythmia monitoring and treatment assembly 102 and the wearable article 400 further comprise a video camera configured to detect the visible information associated with the patient. In implementations, the system further comprises a 3D laser ranging sensor in communication with the video camera and configured for at least one of feature recognition and gesture detection. The patient may rely upon interactions with such sensors to confirm identity and pair the wearable article 400 with the processor 118 of the arrhythmia monitoring and treatment assembly 102. In implementations, touch-based information includes at least one of one or more touches on the remote control, patient fingerprint detection, and repeated taps. In implementations signal-based information includes at least one of an ECG signal detection and biometric sensing for identifying the patient associated with the arrhythmia monitoring and treatment assembly 102 and the wearable article 400 as described in, for example, U.S. Pat. No. 8,271,082 entitled "Medical Device Configured to Test For User Responsiveness," the content of which is incorporated herein by reference. In implementations, audible information includes at least one of voice recognition and receipt of a pass code or phrase.

Figure 7A:
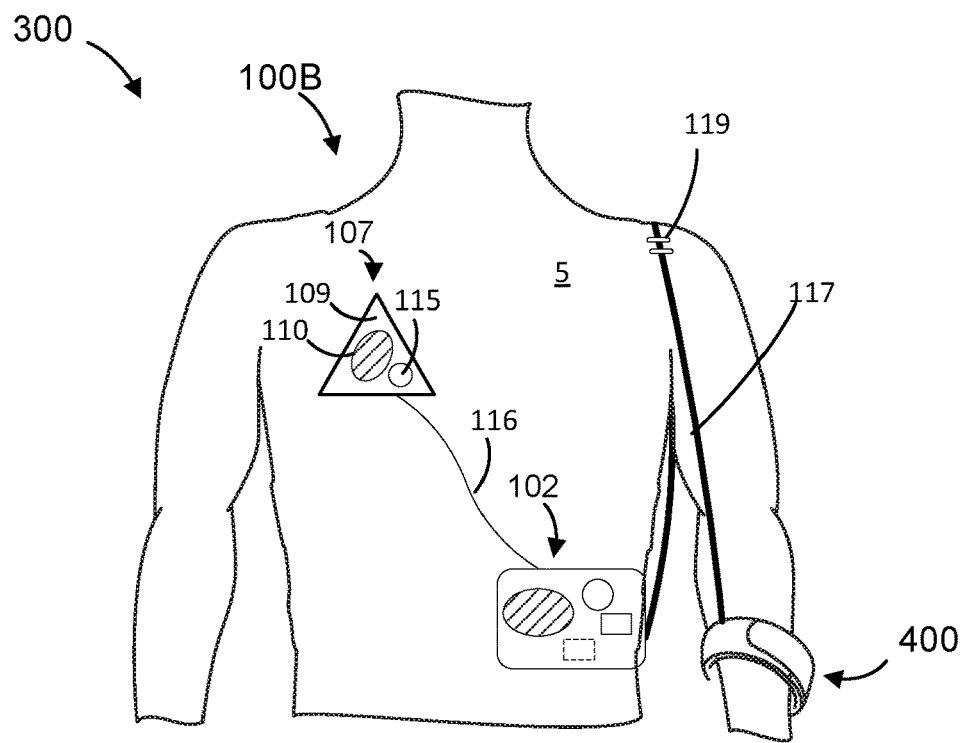
FIG. 7A depicts a schematic of an example cardiac monitoring and treatment system including an adhesively coupled wearable cardiac monitoring and treatment assembly including anterior mounted first and second assemblies and a wearable article in wired communication with the assembly.
Figure 7B:
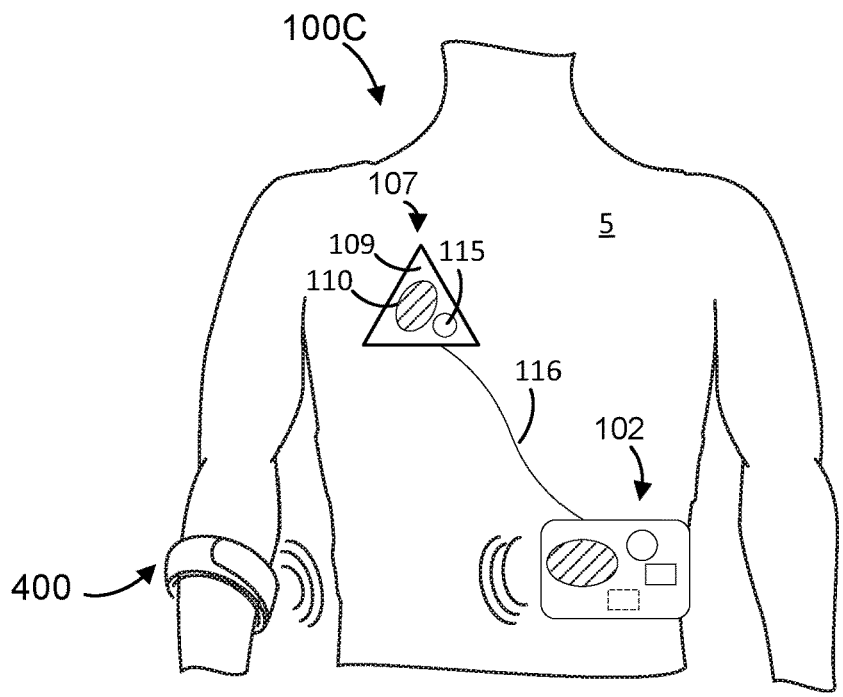
FIG. 7B depicts a schematic of an example cardiac monitoring and treatment system including an adhesively coupled wearable cardiac monitoring and treatment assembly including anterior mounted first and second assemblies and a wearable article in wireless communication with the assembly.

In addition to or alternatively, in implementations, such as those of FIGS. 1A, 7A, and 10, the device 100, including the arrhythmia monitoring and treatment assembly 102, and wearable article 400 are in wired communication, connected by a wire 117. In implementations a wire 117 (e.g., a wired link) extends between the arrhythmia monitoring and treatment assembly 102 and the wearable article 400 such that the communications circuitry (e.g. transceiver 432) and the processor 118 are in wired communication.

Figure 11:
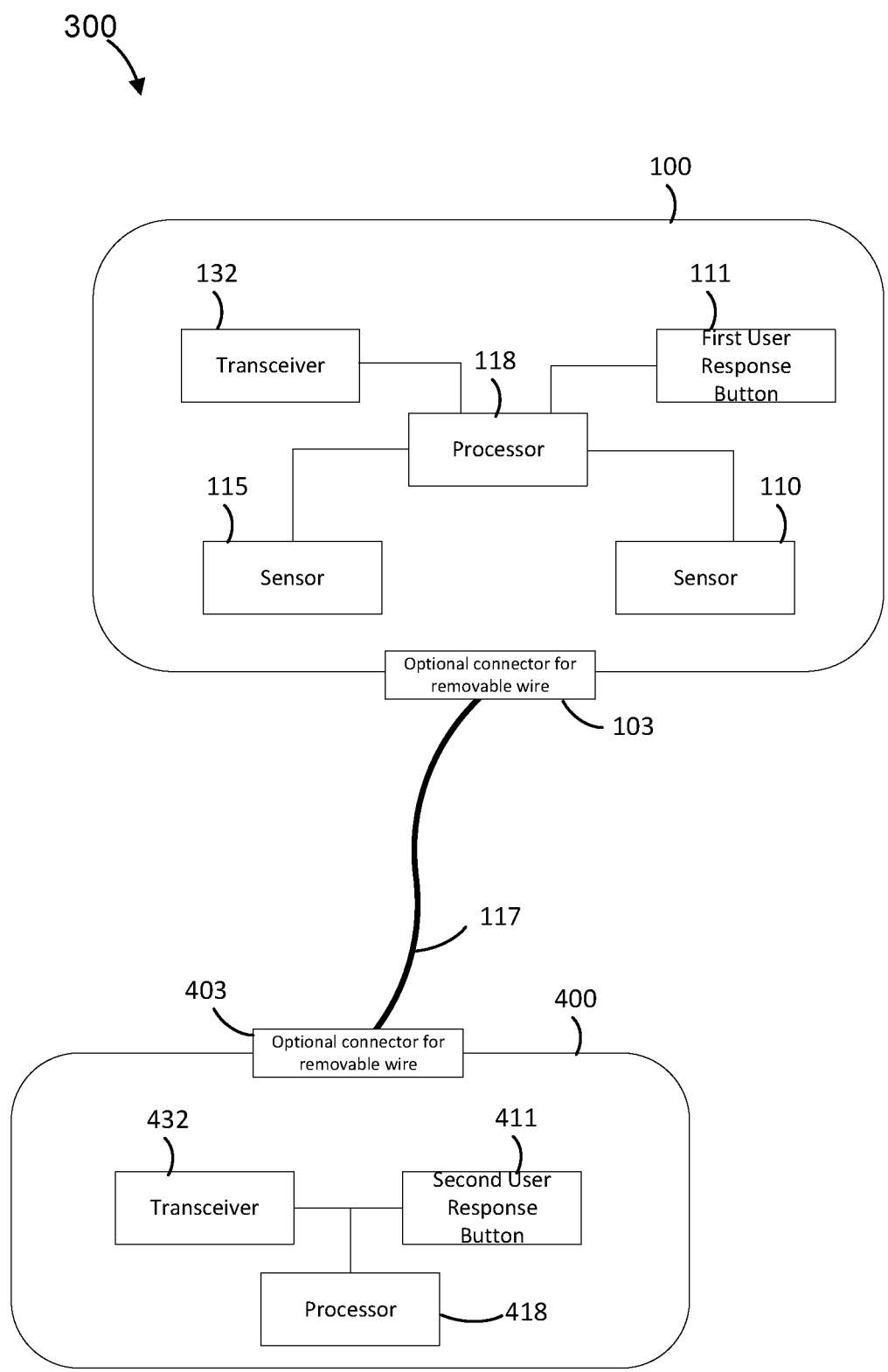
FIG. 11 depicts a schematic of an example cardiac monitoring and treatment system including a wearable cardiac monitoring and treatment device in communication with a wearable article.

In implementations, such as that of FIG. 11, the system can include at least one optionally connected wired communications link (e.g. a wire 117). In implementations, the wire 117 is configured to be detachable from one or both of the arrhythmia monitoring and treatment assembly 102 and the wearable article 400. The system 300 can include a first optional connector 103 for attaching and detaching the removable wire 117 to assembly 102 and a second optional connector 403 for attaching and detaching the removable wire 117 to the wearable article 400. In implementations, the patient wears the device 100 for a short or long term duration and routes a wire 117 from the assembly 102, under their clothing to a wearable article 400 disposed on the body of the patient at an accessible location. For example, as shown in FIG. 7A, the wire 117 is wrapped around the torso 5 of the patient, up the back of the torso 5, over the shoulder, and down the arm of the patient to a wrist worn wearable article 400. The patient can apply medical tape 119 to secure the wire at their shoulder and hold the wire 117 in place and discreetly concealed under clothing. At the end of the day, the patient may wish to remove the wire 117 and/or tape 119. Enabling the patient to selectively and optionally remove the wire 117 and disengage the wired wearable article 400 assists with user compliance in wearing the system 300 for the prescribed duration by improving ease of access to the second at least one user input button throughout waking hours.

Additionally or alternatively, in implementations at least one of the arrhythmia monitoring and treatment assembly 102 and the wearable article 400 further comprises a retractable spool, for example, a ratchet spool and pawl assembly configured to enable the patient to easily and quickly adjust a length of the wire 117 and the amount of tension on the wire and hold the adjusted length position throughout the duration of wear.

As described above with regard to implementations, for example those of FIGS. 8 and 9, the a medical device 100 includes an arrhythmia monitoring and treatment assembly 102 configured to be discreetly worn under one or more articles of clothing. Patients may feel more comfortable complying with continuous wear for a prescribed duration if the arrhythmia monitoring and treatment assembly 102 does not bulge beneath clothing, revealing their private health condition to onlookers. Implementations of the low profile assembly 102 are configured to extend to no more than 10 cm from the skin surface of the patient. This low profile configuration is achieved by sizing and placing various components of the assembly 102 in a compact and comfortably worn arrangement.

In examples, the at least one power source of the arrhythmia monitoring and treatment assembly 102 includes one or more rechargeable batteries configured to be charged by an external battery or power source connectable to a hermetically sealed charging port disposed on the housing 120. In implementations, the batteries have a capacity of 200-300 mAh and are configured to be recharged daily by an external power supply. In implementations, the charging port includes a magnetic assistance for aligning a connector of the external power supply to the charging port. In implementations, the external power supply is configured to be worn discreetly by the patient while charging the battery of the arrhythmia monitoring and treatment assembly 102 such no portion of the assembly 102 requires removal during charging throughout the prescribed duration of wear. In implementations, the wearable support or garment of the device 100 is configured to discreetly house the external power supply configured to be selectively inserted onto the garment or into a pocket of the garment while charging one or more batteries. In implementations, the wearable article 400 comprises the external power supply such that when the wearable article is connected to the device 100, one or more batteries of the device 100 recharge.

In examples, the at least one power source of the arrhythmia monitoring and treatment assembly 102 includes one or more batteries 140 having a combined envelope volume not to exceed one quarter of the volume of the at least one housing 120 and having a capacity of no less than 1200 mAh. In examples, the at least one power source includes one or more batteries having a combined envelope volume not to exceed one quarter of the volume of the at least one housing and having a capacity of 1200 mAh to 8000 mAh. In examples, the at least one battery 140 is configured to provide power to one or more components, such as the one or more capacitors 135. In examples, the battery 140 can include a rechargeable battery or multi-cell battery pack. In examples, the battery 140 can include a non-rechargeable, replaceable battery. In one example implementation, the battery 140 can include three or more 2200 mAh lithium ion cells that provide electrical power to the other components within the device 100. In implementations, the at least one power source comprises at least one 1470 mAh, 3V Lithium ion battery. In examples, the battery 140 can include a plurality of coin cell batteries. In examples, the one or more batteries are flat packed lithium polymer batteries. In examples, the battery 140 can be a flat packed (e.g., prismatic) battery, such as, for example, a lithium ion battery having dimensions ranging between, for example, 12 mm×4 mm×1 mm and 35 mm×50 mm×2 mm. In examples, the at least one power source comprises one or more batteries 140 having a combined volume ranging from about 1 cm$^2$ to 7 cm$^2$ and weighing between about 1 g to 70 g (e.g., 1 g, 5 g, 10 g, 15 g, 20 g, 25 g, 30 g, 40 g, 50 g, 55 g, 60 g, 65 g, 70 g). In examples, the one or more batteries 140 are rechargeable and can provide power output in a range of between 20 mA to 3000 mA and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the device 100 (e.g., defibrillation, pacing, etc.).

It is appreciated that a capacitor 135 of the device 100 may be constructed in a variety of form factors. For example, the capacitor 135 may include an encapsulating rigid enclosure. In implementations, the rigid enclosure can be contoured to conform to the curvature of the torso 5 of the patient thereby resulting in a comfortable, mated fit when worn. For example, the enclosure may be constructed from a rigid plastic including, for example, acrylonitrile butadiene styrene (ABS) plastic with a contoured surface that conforms to the silhouette of a patient. For example, the contoured surface can be configured to conform with a curvature of a portion of the patient's torso, such as lower portion of the torso, an upper anterior portion of the torso, upper posterior portion of the torso, one or more lateral portions of the torso. The particular shape of the contoured surface may be pre-configured or uniquely designed for the patient. For example, various body size measurements may be obtained from the patient and a uniquely tailored enclosure may be 3D printed from, for example, any suitable thermoplastic (e.g., ABS plastic) or any elastomeric and/or flexible 3D printable material.

In some implementations, the capacitor 135 may be compact film capacitor such as a small film capacitor with a maximum thickness of between 1 mm and 40 mm, a capacitance under 700 μF, and a breakdown voltage rating between 500 and 2500 volts. In examples, the capacitor 135 has an envelope volume ranging from about 10 cm$^2$ to 15 cm$^2$. In examples, the capacitor 135 has a 140 microfarad capacity and a voltage rating of at least 1600V. The film capacitor 135 can be manufactured of tightly wound dielectric layers that are compressed and molded to match the silhouette of a patient. For example, the plurality of capacitors can be configured to conform with a curvature of a portion of the patient's torso 5, such as lower portion of the torso, an upper anterior portion of the torso, upper posterior portion of the torso, or one or more lateral portions of the torso. Shaping one or more film capacitors 135 to accommodate one or more contoured regions of a patient's torso 5 increases patient comfort and minimizes bulkiness associated with cylindrical or stacked capacitors. The device 100 therefore can protrude less from the surface of the patients skin that it would if the capacitor had a larger volume and/or less accommodating profile.

As described previously, the one or more batteries 140 can be rechargeable, non-rechargeable, cylindrical, prismatic, and sized for providing energy for one or more defibrillation or pacing charges. Tables 5 and 6 provide example Lithium Ion Prismatic Batteries and Lithium Ion Cylindrical Batteries for use in one or more implementations of short term and long-term wear embodiments of the adhesively coupled device 10, 100:

Lithium Ion Prismatic Battery Examples:

TABLE 5

| Mfgr | Dimensions (mm) | Weight (g) | Nominal Capacity (mAh) | Volume w/ Packing Eff 2 Cells (mL) | Weight 2 Cells (g) | Specific Energy Density 2 Cells (Ah/gL) | Volume w/ Packing Eff 3 Cells (mL) | Weight 3 Cells (g) | Specific Energy Density 3 Cells (Ah/gL) |
|---|---|---|---|---|---|---|---|---|---|
| E-One Moli | 10.8 × 33.9 × 50.2 | 46.5 | 1800 | 38.96395 | 93 | 0.496737 | 58.44593 | 139.5 | 0.220772 |
| E-One Moli | 11.5 × 34 × 50 | 41.5 | 2000 | 41.446 | 83 | 0.581392 | 62.169 | 124.5 | 0.258397 |
| E-One Moli | 11.5 × 34 × 50 | 43 | 2200 | 41.446 | 86 | 0.617222 | 62.169 | 129 | 0.274321 |
| E-One Moli | 10.8 × 34 × 50 | 42 | 2000 | 39.07889 | 84 | 0.609268 | 58.61834 | 126 | 0.270786 |
| Panasonic | 10.5 × 33.8 × 48.5 | 38.3 | 2350 | 36.49082 | 76.6 | 0.840728 | 54.73623 | 114.9 | 0.373657 |
| Panasonic | 10.5 × 33.8 × 48.8 | 38.5 | 2000 | 36.71653 | 77 | 0.70742 | 55.0748 | 115.5 | 0.314409 |

Lithium Ion Cylindrical Battery Examples

TABLE 6

| Mfgr | Dimensions (mm) | Weight (g) | Nominal Capacity (mAh) | Volume w/ Packing Eff 2 Cells (mL) | Weight 2 Cells (g) | Specific Energy Density 2 Cells (Ah/gL) | Volume w/ Packing Eff 3 Cells (mL) | Weight 3 Cells (g) | Specific Energy Density 3 Cells (Ah/gL) |
|---|---|---|---|---|---|---|---|---|---|
| E-One Moli | 18.6 × 65.2 | 46 | 3000 | 40.27 | 92 | 0.810 | 61.32 | 138 | 0.355 |
| E-One Moli | 20.8 × 70.2 | 60 | 3000 | 54.22 | 120 | 0.461 | 82.56 | 180 | 0.202 |
| E-One Moli | 18.4 × 65.2 | 48 | 2400 | 39.41 | 96 | 0.634 | 60.01 | 144 | 0.278 |
| E-One Moli | 18.6 × 65.2 | 50 | 2600 | 40.27 | 100 | 0.646 | 61.32 | 150 | 0.283 |
| E-One Moli | 18.6 × 65.2 | 50 | 2800 | 40.27 | 100 | 0.695 | 61.32 | 150 | 0.304 |
| E-One Moli | 18.4 × 65.2 | 47.5 | 2250 | 39.41 | 95 | 0.601 | 60.01 | 142.5 | 0.263 |
| E-One Moli | 18.6 × 65.2 | 47 | 2000 | 40.27 | 94 | 0.528 | 61.32 | 141 | 0.231 |
| E-One Moli | 18.6 × 65.2 | 47 | 2500 | 40.27 | 94 | 0.660 | 61.32 | 141 | 0.289 |
| Panasonic | 18.5 × 65.3 | 48.5 | 3350 | 39.90 | 97 | 0.866 | 60.75 | 145.5 | 0.379 |
| Panasonic | 18.5 × 65.3 | 48.5 | 3350 | 39.90 | 97 | 0.866 | 60.75 | 145.5 | 0.379 |
| Panasonic | 18.5 × 65.3 | 48 | 3450 | 39.90 | 96 | 0.901 | 60.75 | 144 | 0.394 |
| Panasonic | 18.5 × 65.3 | 48.5 | 2750 | 39.90 | 97 | 0.711 | 60.75 | 145.5 | 0.311 |
| Panasonic | 18.6 × 65.3 | 49 | 2150 | 40.33 | 98 | 0.544 | 61.41 | 147 | 0.238 |
| Panasonic | 18.6 × 65.3 | 49 | 2150 | 40.33 | 98 | 0.544 | 61.41 | 147 | 0.238 |
| Panasonic | 18.6 × 65.3 | 49 | 2500 | 40.33 | 98 | 0.632 | 61.41 | 147 | 0.277 |
| Panasonic | 18.6 × 65.3 | 49 | 1950 | 40.33 | 98 | 0.493 | 61.41 | 147 | 0.216 |
| Panasonic | 18.6 × 65.3 | 49 | 3000 | 40.33 | 98 | 0.759 | 61.41 | 147 | 0.332 |
| Samsung SDI | 18.4 × 65.0 | 48 | 2800 | 39.29 | 96 | 0.742 | 59.82 | 144 | 0.325 |
| Samsung SDI | 18.4 × 65.0 | 44.5 | 2200 | 39.29 | 89 | 0.629 | 59.82 | 133.5 | 0.275 |
| Samsung SDI | 18.4 × 65.0 | 47 | 2600 | 39.29 | 94 | 0.704 | 59.82 | 141 | 0.308 |
| Samsung SDI | 18.4 × 65.0 | 47 | 2600 | 39.29 | 94 | 0.704 | 59.82 | 141 | 0.308 |
| Samsung SDI | 18.40 × 65.0 | 48 | 2950 | 39.29 | 96 | 0.782 | 59.82 | 144 | 0.342 |
| Samsung SDI | 18.40 × 65.0 | 50 | 3200 | 39.29 | 100 | 0.814 | 59.82 | 150 | 0.357 |
| Samsung SDI | 18.33 × 64.85 | 45 | 2500 | 38.90 | 90 | 0.714 | 59.23 | 135 | 0.313 |

In another example, as described previously, in embodiments, the capacitor 135 can be an approximately 140 microfarad, 1600V film capacitor weighing about 118 grams. Alternatively, the capacitor 135 can be a 4 cell cylindrical electrolytic capacitor with a 140 microfarad discharge rating that weighs approximately 400 grams. Similarly, other hardware components can be sized and shaped for compact, lightweight design without impacting performance. For example, the H-Bridge can be in the form of a compact, surface mounted silicon carbide FET (Sic FET) rather than a 4 part IGBT configuration. The ECG acquisition and conditioning circuitry, processor, and therapy delivery circuit can be included on one or more ASICs or one or more wire bonded, epoxy resin protected "chip on board" flip chips.

As described previously with regard to the examples of FIGS. 6A-7B, the arrhythmia monitoring and treatment device 100 includes a first assembly 102 and a separate second assembly 107 coupled to the first assembly 102 and configured to be adhesively coupled to the torso 5 of the patient. The second assembly 107 can be coupled to the first assembly 102 with one or more conductive threads or wires configured for delivering current for an electrical pulse, such as a, for example, a 360 J defibrillation pulse.

The second assembly 107 can include breathable and non-irritating materials and adhesives as described above with regard to the first assembly 102 and pad 105. In examples, the second assembly 107 includes a second one of the plurality of therapy electrodes 110 integrated with a pad 109 of the second assembly 107 and in wired communication with the therapy delivery circuit 130. In examples, the second assembly 107 includes an ECG sensor 115. Because the first assembly 102 contains the therapy delivery circuit, and various other electrical components, the second assembly 107 can be more compact than the first assembly. For example, the second assembly can be a low profile adhesive pad including a therapy electrode 110 and an ECG electrode 115 and having a pad thickness of about 0.1 cm to 2 cm.

In examples, the second assembly 107 includes at least one of a plurality of therapy electrodes 110 integrated with the pad 109. Example therapy electrodes 110 include, for example, conductive metal electrodes, such as those made of stainless steel, tin or aluminum, a conductive ink, or a conductive polymer. In examples, the second assembly can also include at least one of a plurality of ECG sensors 115 integrated with the pad 109. As described with regard to the first assembly 102, the ECG sensors 115 of the second assembly 107 can be non-polarizable ECG electrodes (e.g., clinical grade Ag/AgCl electrodes) or polarizable electrodes (e.g., electrodes having a metal substrate with an oxide layer, such as a $Ta_2O_5$ coating) configured to measure changes in a patient's electrophysiology to measure the patient's ECG information. Example ECG sensors 115 include tantalum pentoxide electrodes, as described in, for example, U.S. Pat. No. 6,253,099 entitled "Cardiac Monitoring Electrode Apparatus and Method," the content of which is incorporated herein by reference. In implementations, the ECG sensors 115 may be made of a core plastic or metal substrate element that is coated with a thick-film polymeric compound filled with a conductive Ag/Ag/Cl metallic filler.

In some examples, at least one therapy electrode 110 and one or more ECG sensors 115 are formed within the pad 109 such that a skin contact surface of each component is coplanar with or protrudes from the patient contact face of the pad 105. In examples, the therapy electrode 110 and the ECG sensors 115 are disposed on the patient contact face of the pad 105. In some implementations, the therapy electrode 114 and ECG sensors 115 are metallic plates (e.g. stainless steel) or substrates that are formed as permanent portions of the second assembly 107. A metallic plate or substrate can be adhered to the pad 109, for example, by a polyurethane adhesive or a polymer dispersion adhesive such as a polyvinyl acetate (PVAc) based adhesive, or other such adhesive. In examples, the ECG sensors 115 are flexible, dry surface electrodes such as, for example, conductive polymer-coated nano-particle loaded polysiloxane electrodes mounted to the pad 109. In some examples, the ECG sensors 115 are flexible, dry surface electrodes such as, for example silver coated conductive polymer foam soft electrodes mounted to the pad 109. In examples, the ECG sensors 115 are screen printed onto the pad 109 with a metallic ink, such as a silver-based ink. In implementations, each of the therapy electrodes 110 has a conductive surface adapted for placement adjacent the patient's skin. In some implementations, the therapy electrodes 110 can include an impedance reducing material and/or mechanism as subsequently described.

In implementations, the at least one therapy electrode 110 and at least one ECG sensor 115 are manufactured as integral components of the pad 109. For example, the therapy electrode 110 and/or the ECG sensor 115 can be formed of the warp and weft of a fabric forming at least a layer of the pad 109. In implementations, the therapy electrode 110 and the ECG sensors 115 are formed from conductive fibers that are interwoven with non-conductive fibers of the fabric.

In examples, the device 100 can include a third assembly (not shown) configured to be adhesively coupled to the torso of a patient. The third pad can include one of the plurality of therapy electrodes 110 integrated with a pad of the third assembly and in wired communication with the therapy delivery circuit 130. The third assembly can have similar characteristics as those described above with regard to the second assembly 107. In examples, the third pad can be configured for adhesively attaching to a posterior portion of the torso 5 of the patient, between the shoulder blades of the patient, for example, while the first assembly 102 is positioned along the lower ridge of the rib cage and the second assembly 107 is positioned on an upper anterior portion of the torso 5 adjacent to the apex of the heart. In examples, the third assembly include a third pad configured to be adhesively coupled to the torso of the patient adjacent the atria In implementations, the device 100 may include gel deployment circuitry configured to cause the delivery of conductive gel substantially proximate to a treatment site (e.g., a surface of the patient's skin in contact with the therapy electrode 114) prior to delivering therapeutic shocks to the treatment site. As described in U.S. Pat. No. 9,008,801, titled "WEARABLE THERAPUETIC DEVICE," issued on Apr. 14, 2015 (hereinafter the "'801 patent"), which is hereby incorporated herein by reference in its entirety, the gel deployment circuitry may be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry may be coupled to or integrated within a therapy electrode 110 or other therapy delivery device as a single unit. When a treatable cardiac condition is detected and no patient response is received after device prompting, the gel deployment circuitry can be signaled to deploy the conductive gel. In some examples, the gel deployment circuitry may be constructed as one or more separate and independent gel deployment modules. Such modules may be configured to receive removable and/or replaceable gel cartridges (e.g., cartridges that contain one or more conductive gel reservoirs). As such, the gel deployment circuitry may be permanently disposed in the device as part of a therapy delivery circuit 130, while the cartridges may be removable and/or replaceable. Such gel deployment circuitry can be coupled to or integrated within a first assembly 102 a second assembly 107 and/or a third assembly of the device.

When a treatable cardiac condition is detected and no patient response is received after device prompting, the gel deployment circuitry can be signaled to deploy the conductive gel. In some examples, the gel deployment circuitry can be constructed as one or more separate and independent gel deployment modules. Such modules can be configured to receive removable and/or replaceable gel cartridges (e.g., cartridges that contain one or more conductive gel reservoirs). As such, the gel deployment circuitry can be permanently disposed in the device as part of the therapy delivery systems, while the cartridges can be removable and/or replaceable.

In some implementations, the gel deployment modules can be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry can be removable and/or replaceable. In some examples, the gel deployment pack, including the one or more gel reservoirs and associated gel deployment circuitry, and the therapy electrode can be integrated into a therapy electrode assembly that can be removed and replaced as a single unit either after use, or if damaged or broken.

As described above, the teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, and other similar wearable medical devices.

A wearable medical cardiac monitoring device is capable of continuous use by the patient. Further, the wearable medical device can be configured as a long-term or extended use medical device. Such devices can be designed to be used by the patient for a long period of time, for example, a period of 24 hours or more, several days, weeks, months, or even years. Accordingly, the long period of use can be uninterrupted until a physician or other caregiver provides specific prescription to the patient to stop use of the wearable medical device. For example, the wearable medical device can be prescribed for use by a patient for a period of at least one week. In an example, the wearable medical device can be prescribed for use by a patient for a period of at least 30 days. In an example, the wearable medical device can be prescribed for use by a patient for a period of at least one month. In an example, the wearable medical device can be prescribed for use by a patient for a period of at least two months. In an example, the wearable medical device can be prescribed for use by a patient for a period of at least three months. In an example, the wearable medical device can be prescribed for use by a patient for a period of at least six months. In an example, the wearable medical device can be prescribed for use by a patient for a long period of at least one year. In some implementations, the extended use can be uninterrupted until a physician or other caregiver provides specific instruction to the patient to stop use of the wearable medical device.

Implementations of an adhesively coupled wearable device can include additional wearable supports and/or support garments for offsetting one or more forces such as peel forces, shear forces, cleavage forces and tensile forces and retaining the wearable device in contact with the torso of the patient. In such implementations, the wearable supports and/or support garments assist with preventing the wearable device from pulling on the skin of the patient and therefore increase and/or ensure patient comfort throughout the duration of wear. Ensuring patient comfort removes an impediment to patient compliance with wearing the device throughout the prescribed durations. Such wearable supports and/or support garments can be especially beneficial during long-term durations of prescribed wear.

Regardless of the period of wear, the use of the wearable medical device can include continuous or nearly continuous wear by the patient as previously described. For example, the continuous use can include continuous wear or attachment of the wearable medical device to the patient. In implementations, the continuous attachment is through one or more of the electrodes as described herein during both periods of monitoring and periods when the device may not be monitoring the patient but is otherwise still worn by or otherwise attached to the patient. Continuous use can include continuously monitoring the patient while the patient is wearing the device for cardiac-related information (e.g., electrocardiogram (ECG) information, including arrhythmia information, cardiac vibrations, etc.) and/or non-cardiac information (e.g., blood oxygen, the patient's temperature, glucose levels, tissue fluid levels, and/or pulmonary vibrations). For example, the wearable medical device can carry out its continuous monitoring and/or recording in periodic or aperiodic time intervals or times (e.g., every few minutes, hours, once a day, once a week, or other interval set by a technician or prescribed by a caregiver). Alternatively or additionally, the monitoring and/or recording during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

In implementations, the patient-worn arrhythmia monitoring and treatment device 100 further includes a patient notification output. In response to detecting one or more treatable arrhythmia conditions, the processor 118 is configured to prompt the patient for a response by issuing the patient notification output, which may be an audible output, tactile output, visual output, or some combination of any and all of these types of notification outputs. In the absence of a response to the notification output from the patient, the processor is configured to cause the therapy delivery circuit 130 to deliver the one or more therapeutic pulses to the patient.

Figure 12:
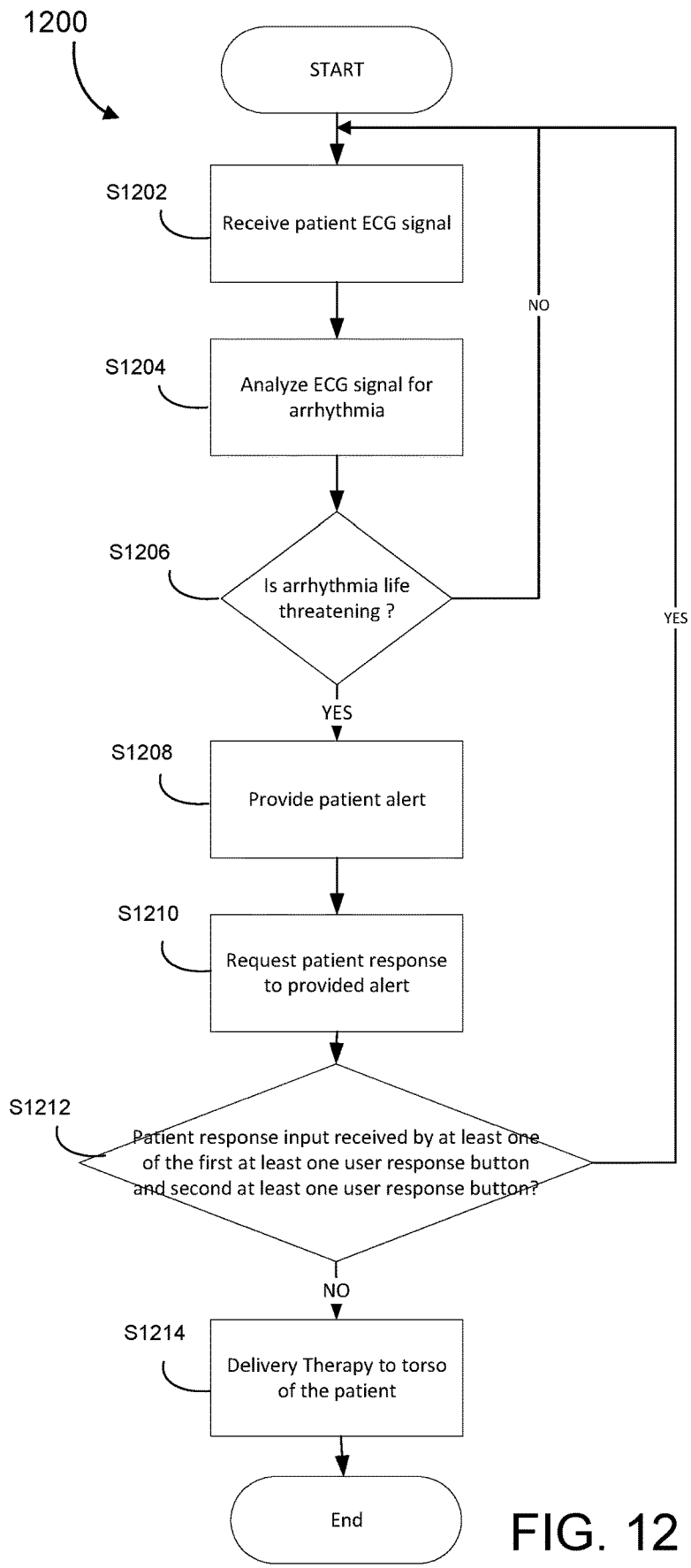
FIG. 12 is a schematic of an example method of using a cardiac monitoring and treatment system including a wearable cardiac monitoring and treatment device in communication with a wearable article.

FIG. 12 depicts an example of a process 1200 for determining whether to initiate a therapy sequence and apply a therapeutic pulse to the body of a patient. In implementations, the processor 118, receives S1202 a patient ECG signal from the therapy electrodes 114 and analyzes S1204 the ECG signal for an arrhythmia condition. The processor 118 determines S1206 whether the arrhythmia is life threatening condition and requires treatment. If the arrhythmia is not life threatening, the processor 118 can cause a portion of the ECG signal to be stored in memory for later analysis and continue to monitor the patient ECG signal. If the arrhythmia is life threatening, the processor provides S1208 a patient notification output and requests S1210 a patient response to the provided notification output. In implementations, the patient responds to an alert by interacting with a user interface (e.g., the user interface 208 of FIG. 13), which includes, for example, one or more buttons (e.g. the first at least one button 111 of the device, as shown in FIGS. 1A, 6C, 8, and 9) or touch screen interface buttons with haptic feedback (e.g., touch screen buttons on the user interface 208 of the housing 120 and/or the second at least one button 411 of the wearable article 400 or like devices, such as smartphones running user-facing interactive applications.). The response may be, for example, pressing one or more buttons in a particular sequence or for a particular duration. The processor 118 determines S1212 whether the patient response was received. If the patient responds to the notification output, the processor 118 is notified that the patient is conscious and returns to a monitoring mode. If the patient is unconscious and unable to respond to the provided alert, the processor 118 initiates S1214 the therapy sequence and treats S1216 the patient with the delivery of energy to the body of the patient.

In implementations, a method of treating a cardiac arrhythmia, includes providing an arrhythmia monitoring and treatment device configured to be worn on the torso of the patient so as to be at least partially concealed under clothing of a patient, wherein the device is configured for providing therapy to the patient on detecting one or more arrhythmia conditions of the patient. The device comprises a plurality of ECG sensing electrodes and associated circuitry configured to monitor an ECG signal of the patient, and a first at least one user response button disposed on the arrhythmia monitoring and treatment assembly at a first location on the patient's torso such that the first at least one user response button is concealed under clothing of the patient. The device includes a processor in communication with the first at least one user response button and the plurality of ECG sensing electrodes and associated circuitry. The method includes providing a second at least one user response button configured to be worn on a second location of the patient's body at a location other than the torso such that the second at least one user response button is accessible to the patient, and the second at least one user response button is in communication with the processor.

As described previously with regard to implementations, the processor analyzes an ECG signal of the patient received via the an arrhythmia monitoring and treatment device to detect the one or more arrhythmia conditions of the patient and causes the arrhythmia monitoring and treatment assembly to provide a warning of an impending therapy to be delivered to the patient in response to the detected one or more arrhythmia conditions of the patient. As described with regard to FIG. 12, if the processor receives from at least one of the first and second at least one user response buttons a user input in response to the warning of the impending therapy, the processor suspends the impending therapy delivery to the body of the patient. In implementations, if the second at least one user response button is pressed for longer than a threshold duration (e.g. longer than 5 seconds), the processor instructs the device to prompt the patient to release the button. If the second at least one user response button is not released the device will return to a state of imminent therapy delivery and will alert the patient to the imminent shock. In implementations in which the second at least one user response button is pressed for longer than a threshold duration (e.g. the user has fallen and landed with their hand pressing the second at least one user response button), the processor 118 may require a patient press the first at least one user response button to delay therapy if the patient is conscious and unable to remove a hand from touching the readily accessible wearable article.

In implementations, if the first at least one user response button 311 and/or second at least one user response button is pressed for longer than a threshold duration without release, the device 10, 100 may prompt the user to indicate consciousness. For example, the device 100 may vibrate, prompting the user to tap the housing 120 of the device with one or more taps in an act of conscious volition to stop the vibration. The device may include a second, repeated vibration prompt to ensure that the user is conscious by requiring the receipt of a second one or more taps to the housing 120 to stop the vibration. An accelerometer or other sensor comprised in the housing can detect the one or more user taps to the housing.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device can be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

FIGS. 1 through 11 illustrate example medical devices 10 (e.g. devices 10A-10G), 100 that are external, ambulatory, and wearable by a patient, and configured to implement one or more configurations described herein. For example, the medical device 10, 100 can be a non-invasive medical device configured to be located substantially external to the patient. Such a medical device can be, for example, an ambulatory medical device that is capable of and designed for moving with the patient as the patient goes about his or her daily routine. The example medical devices as described herein can be bodily-attached to the patient via an adhesive pad and/or via a wearable support and/or support garment worn about the torso of the patient. For example, the medical device can be a wearable cardioverter defibrillator. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses. In some implementations, the medical devices 10, 100 may be prescribed for long-term duration of wear and include a wearable support and/or support garment. In some implementations of the medical devices 10, 100 may be prescribed for short-term durations of wear and rely only on adhesives without the need for one or more additional wearable supports and/or support garments to provide reliability and patient comfort throughout the duration of wear.

In examples, the medical device can include physiological sensors configured to detect one or more cardiac signals. Examples of such signals include ECG signals and/or other sensed cardiac physiological signals from the patient. In certain implementations, the physiological sensors can include additional components such as accelerometers, vibrational sensors, and other measuring devices for recording additional parameters. For example, the physiological sensors can also be configured to detect other types of patient physiological parameters and vibrational signals, such as tissue fluid levels, cardio-vibrations, pulmonary-vibrations, respiration-related vibrations of anatomical features in the airway path, patient movement, etc. Example physiological sensors can include ECG sensors including a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference.

In examples, the physiological sensors can include a heart rate sensor for detecting heart beats and monitoring the heart rate of the patient. For instance, such heart rate sensors can include the ECG sensors and associated circuitry described above. In some examples, the heart rate sensors can include a radio frequency based pulse detection sensor or a pulse oximetry sensor worn adjacent an artery of the patient. In implementations, the heart rate sensor can be worn about the wrist of a patient, for example, incorporated on and/or within a watch or a bracelet. In some examples, the heart rate sensor can be integrated within a patch adhesively coupled to the skin of the patient over an artery.

In some examples, the therapy electrodes 110 can also be configured to include sensors configured to detect ECG signals as well as other physiological signals of the patient. The ECG data acquisition and conditioning circuitry 125 is configured to amplify, filter, and digitize these cardiac signals. One or more of the therapy electrodes 110 can be configured to deliver one or more therapeutic defibrillating shocks to the body of the patient when the medical device 100 determines that such treatment is warranted based on the signals detected by the ECG sensors 115 and processed by the processor 118. Example therapy electrodes 110 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). The therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 13:
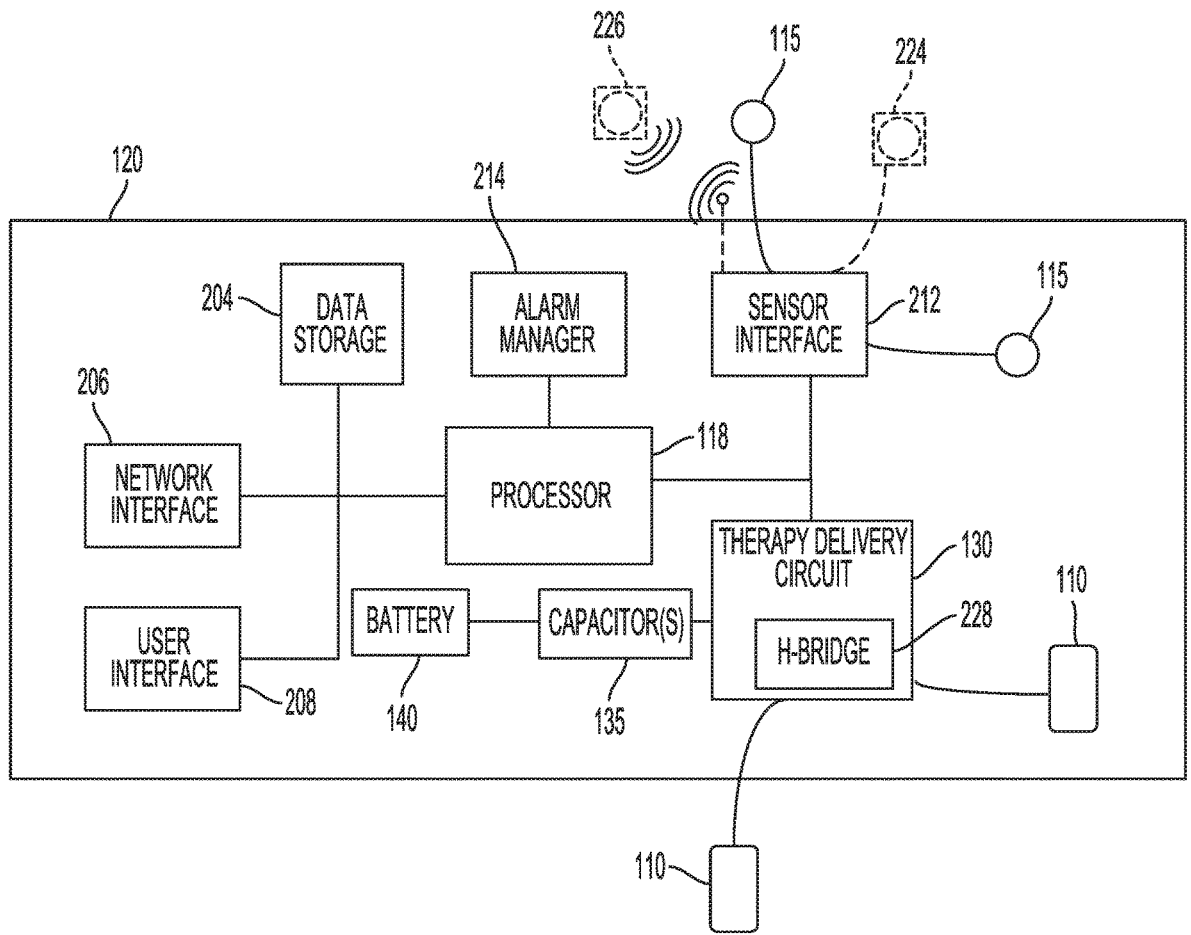
FIG. 13 depicts a schematic diagram of an embodiment of an adhesively coupled wearable cardiac monitoring and treatment device of a cardiac monitoring and treatment system.

FIG. 13 illustrates an example component-level view of the medical device. As shown in FIG. 13, the medical device housing 120 can include a therapy delivery circuit 130 including a polarity switching component such as an H-bridge 228, a data storage 204, a network interface 206, a user interface 208 at least one battery 140, a sensor interface 212 that includes, for example, an ECG data acquisition and conditioning circuit 125, an alarm manager 214, least one processor 118, and one or more capacitors 135. A patient monitoring medical device can include components like those described with regard to FIG. 13, but does not include the therapy delivery circuit 130. Alternatively, a patient monitoring medical device can include components like those described with regard to FIG. 13, but includes a switching mechanism for rendering the therapy delivery circuit 130 inoperative.

The therapy delivery circuit 130 is coupled to two or more therapy electrodes 110 configured to provide therapy to the patient. As indicated in FIG. 13, in examples, at least one of the two or more therapy electrodes 110 is within the housing 120 and another of the two or more therapy electrodes 110 is remote from the housing 120. For example, the therapy delivery circuit 130 includes, or is operably connected to, circuitry components that are configured to generate and provide the therapeutic shock. The circuitry components include, for example, resistors, one or more capacitors, relays and/or switches, an electrical bridge such as an H-bridge 228 (e.g., an H-bridge including a plurality of insulated gate bipolar transistors or IGBTs that deliver and truncate a therapy pulse), voltage and/or current measuring components, and other similar circuitry arranged and connected such that the circuitry work in concert with the therapy delivery circuit and under control of one or more processors (e.g., processor 118) to provide, for example, one or more pacing or defibrillation therapeutic pulses.

Pacing pulses can be used to treat cardiac arrhythmias such as bradycardia (e.g., in some implementations, less than 30 beats per minute) and tachycardia (e.g., in some implementations, more than 150 beats per minute) using, for example, fixed rate pacing, demand pacing, anti-tachycardia pacing, and the like. Defibrillation pulses can be used to treat ventricular tachycardia and/or ventricular fibrillation.

In implementations, each of the therapy electrodes 110 has a conductive surface adapted for placement adjacent the patient's skin and has an impedance reducing means contained therein or thereon for reducing the impedance between a therapy electrode and the patient's skin. As previously described with regard to implementations, each of the therapy electrodes can include a conductive impedance reducing adhesive layer, such as a breathable anisotropic conductive hydrogel disposed between the therapy electrodes and the torso of the patient. In implementations, the adhesively coupled patient-worn arrhythmia monitoring and treatment device 100 may include gel deployment circuitry configured to cause the delivery of conductive gel substantially proximate to a treatment site (e.g., a surface of the patient's skin in contact with the therapy electrode 110) prior to delivering therapeutic shocks to the treatment site. As described in U.S. Pat. No. 9,008,801, titled "WEARABLE THERAPUETIC DEVICE," issued on Apr. 14, 2015 (hereinafter the "'801 patent"), which is incorporated herein by reference in its entirety, the gel deployment circuitry can be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry can be coupled to or integrated within a first assembly 102, a second assembly 107 and/or a third assembly of the device.

When a treatable cardiac condition is detected and no patient response is received after device prompting, the gel deployment circuitry can be signaled to deploy the conductive gel. In some examples, the gel deployment circuitry can be constructed as one or more separate and independent gel deployment modules. Such modules can be configured to receive removable and/or replaceable gel cartridges (e.g., cartridges that contain one or more conductive gel reservoirs). As such, the gel deployment circuitry can be permanently disposed in the device as part of the therapy delivery systems, while the cartridges can be removable and/or replaceable.

In some implementations, the gel deployment modules can be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry can be removable and/or replaceable. In some examples, the gel deployment pack, including the one or more gel reservoirs and associated gel deployment circuitry, and the therapy electrode can be integrated into a therapy electrode assembly that can be removed and replaced as a single unit either after use, or if damaged or broken.

Figure 14:
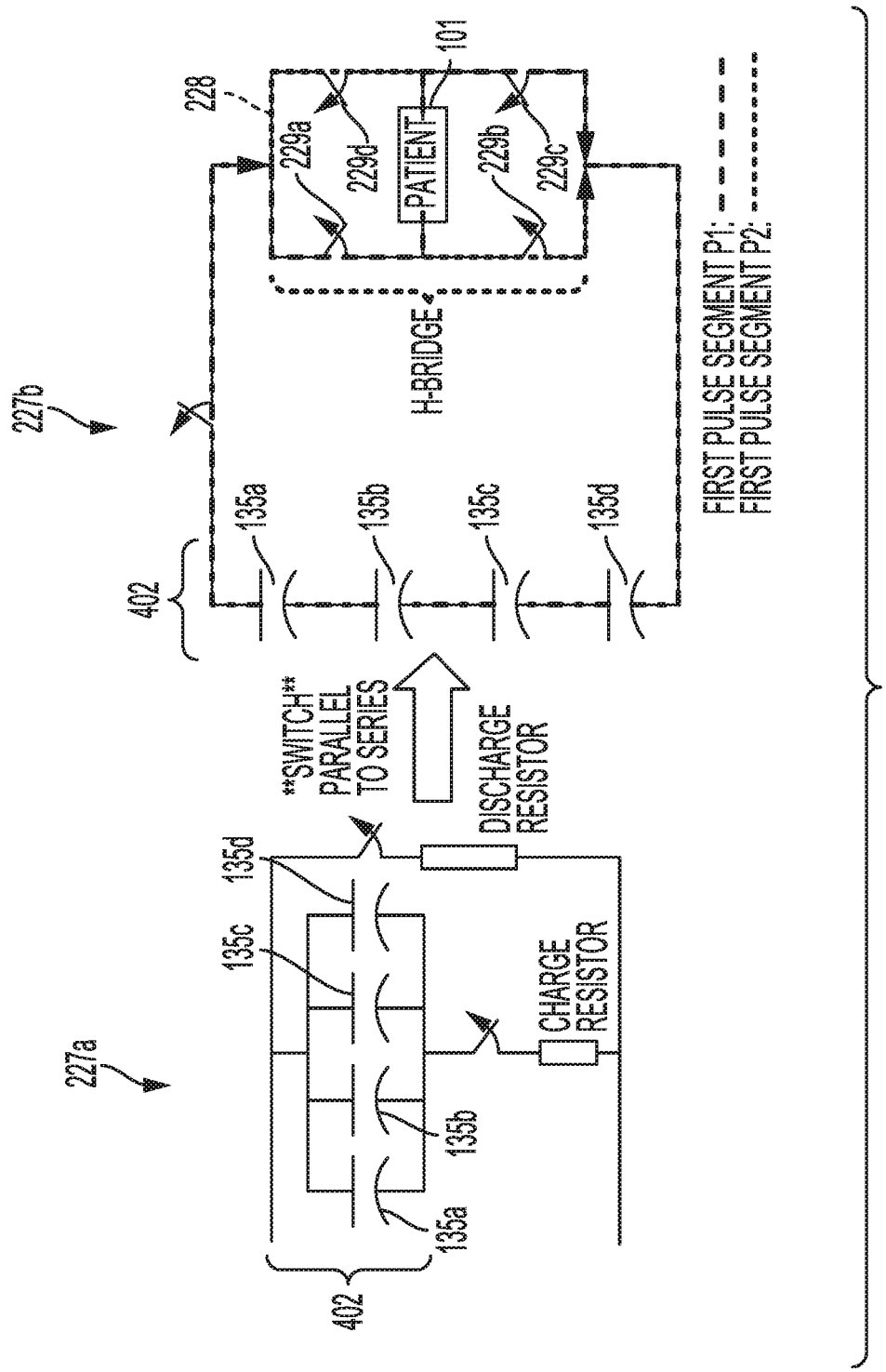
FIG. 14 depicts a schematic diagram of an embodiment of electrical components of an adhesively coupled wearable cardiac monitoring and treatment device of a cardiac monitoring and treatment system.

Continuing with the description of the example medical device of FIG. 13, in implementations, the one or more capacitors 135 is a plurality of capacitors (e.g., two, three, four or more capacitors) comprising a capacitor bank 402, as shown in FIG. 14. These capacitors 135 can be switched into a series connection during discharge for a defibrillation pulse. For example, four capacitors of approximately 650 g can be used. In one implementation, the capacitors can have between 200 to 2500 volt surge rating and can be charged in approximately 5 to 30 seconds from a battery 140 depending on the amount of energy to be delivered to the patient. Additional implementations of capacitor properties and arrangements on a patient-worn medical device are provided herein in subsequent sections.

For example, each defibrillation pulse can deliver between 60 to 400 joules (J) of energy. In some implementations, the defibrillating pulse can be a biphasic truncated exponential waveform, whereby the signal can switch between a positive and a negative portion (e.g., charge directions). An amplitude and a width of the two phases of the energy waveform can be automatically adjusted to deliver a predetermined energy amount.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device. In certain implementations, the data storage 204 can include executable instructions that, when executed, are configured to cause the processor 118 to perform one or more functions.

In some examples, the network interface 206 can facilitate the communication of information between the medical device and one or more other devices or entities over a communications network. For example, the network interface 206 can be configured to communicate with a remote computing device such as a remote server or other similar computing device. The network interface 206 can include communications circuitry for transmitting data in accordance with a BLUETOOTH wireless standard for exchanging such data over short distances to an intermediary device(s) (e.g., a base station, a "hotspot" device, a smartphone, a tablet, a portable computing device, and/or other devices in proximity of the wearable medical device 100). The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a WI-FI communications link based on the IEEE 802.11 standard.

In certain implementations, the user interface 208 can include one or more physical interface devices such as input devices, output devices, and combination input/output devices and a software stack configured to drive operation of the devices. These user interface elements may render visual, audio, and/or tactile content. Thus, the user interface 208 may receive input or provide output, thereby enabling a user to interact with the medical device. In some implementations, the user interface 208 can be implemented as a wearable article or as a hand-held user interface device. (See, for example, wearable articles including the patient interface pod 40 of FIG. 2 and the wrist and arm worn remote devices 400 of FIGS. 1A-B, and 7A-10.) For instance, the hand-held user interface device can be a smartphone or other portable device configured to communicate with the processor 118 via the network interface 206. In an implementation, the hand-held user interface device may also be the intermediary device for facilitating the transfer of information from the device to a remote server.

As described, the medical device can also include at least one battery 140 configured to provide power to one or more components, such as the one or more capacitors 135. The battery 140 can include a rechargeable multi-cell battery pack. In one example implementation, the battery 140 can include three or more 2200 mAh lithium ion cells that provide electrical power to the other device components. For example, the battery 140 can provide its power output in a range of between 20 mA to 1000 mA (e.g., 40 mA) output and can support 24 hours, 48 hours, 72 hours, or more, of runtime between charges. As previously descried in detail, in certain implementations, the battery capacity, runtime, and type (e.g., lithium ion, nickel-cadmium, or nickel-metal hydride) can be changed to best fit the specific application of the medical device.

The sensor interface 212 can be coupled to one or more sensors configured to monitor one or more physiological parameters of the patient. As shown in FIG. 13 the sensors can be coupled to the medical device controller (e.g., processor 118) via a wired or wireless connection. The sensors can include one or more sensing electrodes (e.g., ECG sensors 115), vibrations sensors 224, and tissue fluid monitors 226 (e.g., based on ultra-wide band radiofrequency devices). For example, the sensor interface 212 can include ECG circuitry (such as ECG acquisition and conditioning circuitry 125 of FIGS. 8 and 9) and/or accelerometer circuitry, which are each configured to receive and condition the respective sensor signals.

The sensing electrodes can monitor, for example, a patient's ECG information. For example, the sensing electrodes of FIG. 13 can be ECG sensors 115 and can include conductive electrodes with stored gel deployment (e.g., metallic electrodes with stored conductive gel configured to be dispersed in the electrode-skin interface when needed), conductive electrodes with a conductive adhesive layer, or dry electrodes (e.g., a metallic substrate with an oxide layer in direct contact with the patient's skin). The sensing electrodes can be configured to measure the patient's ECG signals. The sensing electrodes can transmit information descriptive of the ECG signals to the sensor interface 212 for subsequent analysis.

The vibrations sensors 224 can detect a patient's cardiac or pulmonary (cardiopulmonary) vibration information. For example, the cardiopulmonary vibrations sensors 224 can be configured to detect cardio-vibrational biomarkers in a cardio-vibrational signal, including any one or all of S1, S2, S3, and S4 cardio-vibrational biomarkers. From these cardio-vibrational biomarkers, certain electromechanical metrics can be calculated, including any one or more of electromechanical activation time (EMAT), percentage of EMAT (% EMAT), systolic dysfunction index (SDI), left ventricular diastolic perfusion time (LDPT), and left ventricular systolic time (LVST). The cardiopulmonary vibrations sensors 224 may also be configured to detect hear wall motion, for example, by placement of the sensor 224 in the region of the apical beat.

The vibrations sensors 224 can include an acoustic sensor configured to detect vibrations from a subject's cardiac or pulmonary (cardiopulmonary) system and provide an output signal responsive to the detected vibrations of the targeted organ. For instance, in some implementations, the vibrations sensors 224 are able to detect vibrations generated in the trachea or lungs due to the flow of air during breathing. The vibrations sensors 224 can also include a multi-channel accelerometer, for example, a three channel accelerometer configured to sense movement in each of three orthogonal axes such that patient movement/body position can be detected. The vibrations sensors 224 can transmit information descriptive of the cardiopulmonary vibrations information or patient position/movement to the sensor interface 212 for subsequent analysis.

The tissue fluid monitors 226 can use radio frequency (RF) based techniques to assess changes of accumulated fluid levels over time. For example, the tissue fluid monitors 226 can be configured to measure fluid content in the lungs (e.g., time-varying changes and absolute levels), for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the processor 118 to an appropriate component within the medical device. For example, if cardiac data is collected by the cardiopulmonary vibrations sensor 224 and transmitted to the sensor interface 212, the sensor interface 212 can transmit the data to the processor 118 which, in turn, relays the data to a cardiac event detector. The cardiac event data can also be stored on the data storage 204.

An alarm manager 214 can be configured to manage alarm profiles and notify one or more intended recipients of events specified within the alarm profiles as being of interest to the intended recipients. These intended recipients can include external entities such as users (e.g., patients, physicians, other caregivers, patient care representatives, and other authorized monitoring personnel) as well as computer systems (e.g., monitoring systems or emergency response systems). The alarm manager 214 can be implemented using hardware or a combination of hardware and software. For instance, in some examples, the alarm manager 214 can be implemented as a software component that is stored within the data storage 204 and executed by the processor 118. In this example, the instructions included in the alarm manager 214 can cause the processor 118 to configure alarm profiles and notify intended recipients according to the configured alarm profiles. In some examples, alarm manager 214 can be an application-specific integrated circuit (ASIC) that is coupled to the processor 118 and configured to manage alarm profiles and notify intended recipients using alarms specified within the alarm profiles. Thus, examples of alarm manager 214 are not limited to a particular hardware or software implementation.

In some implementations, the processor 118 includes one or more processors (or one or more processor cores) that each are configured to perform a series of instructions that result in manipulated data and/or control the operation of the other components of the medical device. In some implementations, when executing a specific process (e.g., cardiac monitoring), the processor 118 can be configured to make specific logic-based determinations based on input data received, and be further configured to provide one or more outputs that can be used to control or otherwise inform subsequent processing to be carried out by the processor 118 and/or other processors or circuitry with which processor 118 is communicatively coupled. Thus, the processor 118 reacts to a specific input stimulus in a specific way and generates a corresponding output based on that input stimulus. In some example cases, the processor 118 can proceed through a sequence of logical transitions in which various internal register states and/or other bit cell states internal or external to the processor 118 can be set to logic high or logic low. The processor 118 can be configured to execute a function stored in software. For example, such software can be stored in a data store coupled to the processor 118 and configured to cause the processor 118 to proceed through a sequence of various logic decisions that result in the function being executed. The various components that are described herein as being executable by the processor 118 can be implemented in various forms of specialized hardware, software, or a combination thereof. For example, the processor can be a digital signal processor (DSP) such as a 24-bit DSP processor. The processor 118 can be a multi-core processor, e.g., a processor having two or more processing cores. The processor can be an Advanced RISC Machine (ARM) processor such as a 32-bit ARM processor or a 64-bit ARM processor. The processor can execute an embedded operating system and include services provided by the operating system that can be used for file system manipulation, display & audio generation, basic networking, firewalling, data encryption and communications.

In implementations, the therapy delivery circuit 130 includes, or is operably connected to, circuitry components that are configured to generate and provide the therapeutic shock. As described previously, the circuitry components include, for example, resistors, one or more capacitors 135, relays and/or switches, an electrical bridge such as an H-bridge 228 (e.g., an H-bridge circuit including a plurality of switches, (e.g. insulated gate bipolar transistors or IGBTs, silicon carbide field effect transistors (SiC FETs), metal-oxide semiconductor field effect transistors (MOSFETS), silicon-controlled rectifiers (SCRs), or other high current switching devices)), voltage and/or current measuring components, and other similar circuitry components arranged and connected such that the circuitry components work in concert with the therapy delivery circuit 130 and under control of one or more processors (e.g., processor 118) to provide, for example, one or more pacing or defibrillation therapeutic pulses.

In implementations, the device 100 further includes a source of electrical energy, for example, the one or more capacitors 135, that stores and provides energy to the therapy delivery circuit 130. The one or more therapeutic pulses are defibrillation pulses of electrical energy, and the one or more treatable arrhythmias include ventricular fibrillation and ventricular tachycardia. In implementations, the one or more therapeutic pulses are biphasic exponential pulses. Such therapeutic pulses can be generated by charging the one or more capacitors 135 and discharging the energy stored in the one or more capacitors 135 into the patient. For example, the therapy delivery circuit 130 can include one or more power converters for controlling the charging and discharging of the one or more capacitors 135. In some implementations, the discharge of energy from the one or more capacitors 135 can be controlled by, for example, an H-bridge that controls the discharge of energy into the body of the patient, like the H-bridge circuit described in U.S. Pat. No. 6,280,461, titled "PATIENT-WORN ENERGY DELIVERY APPARATUS," issued on Aug. 28, 2001, and U.S. Pat. No. 8,909,335, titled "METHOD AND APPARATUS FOR APPLYING A RECTILINEAR BIPHASIC POWER WAVEFORM TO A LOAD," issued on Dec. 9, 2014, each of which is hereby incorporated herein by reference in its entirety.

As shown in the embodiment to FIG. 14, the H-bridge 228 is electrically coupled to a capacitor bank 402 including four capacitors 135*a-d* that are charged in parallel at a preparation phase 227*a* and discharged in series at a treatment phase 227*b*. In some implementations, the capacitor bank 402 can include more or fewer than four capacitors 135. During the treatment phase 227*b*, the H-bridge 228 applies a therapeutic pulse that causes current to flow through the torso 5 of the patient in desired directions for desired durations. The H-bridge 228 includes H-bridge switches 229*a-d* that are opened and closed selectively by a switching transistor such as insulated gate bipolar transistors (IGBTs), silicon carbide field effect transistors (SiC FETs), metal-oxide semiconductor field effect transistors (MOSFETS), silicon-controlled rectifiers (SCRs), or other high current switching devices. Switching a pair of transistors to a closed position, for example switches 229*a* and 229*c*, enables current to flow in a first direction for first pulse segment P1. Opening switches 229*a* and 229*c* and closing switches 229*b* and 229*d* enables current to flow through the torso 5 of the patient in a second pulse segment P2 directionally opposite the flow of the first pulse segment P1.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A system for providing a patient with arrhythmia treatment that is worn partially under clothing of the patient, comprising:

an arrhythmia monitoring and treatment assembly configured to be worn on a torso of the patient and discreetly extending from a skin surface of the patient, the arrhythmia monitoring and treatment assembly comprising a housing having a tallest height extending no more than 10 cm from the skin surface of the patient, wherein the arrhythmia monitoring and treatment assembly further comprises at least one pad configured to be adhesively attached to the patient's torso, and the housing is configured to be mounted on the at least one pad, and wherein the arrhythmia monitoring and treatment assembly is configured for providing therapy to the patient on detecting one or more arrhythmia conditions of the patient;

first two user response buttons disposed on the housing of the arrhythmia monitoring and treatment assembly having the tallest height extending no more than 10 cm from the skin surface of the patient at a first location on the patient's torso such that the first two user response buttons are configured to be concealed under the clothing of the patient, wherein the first two user response buttons are disposed on the housing such that the patient must press the first two user response buttons simultaneously with two fingers;

a second at least one user response button configured to be worn on a second location of the patient's body at a location other than the torso such that the second at least one user response button is accessible to the patient; and a processor disposed in the arrhythmia monitoring and treatment assembly configured to analyze an ECG signal of the patient received via the arrhythmia monitoring and treatment assembly to detect the one or more arrhythmia conditions of the patient, cause the arrhythmia monitoring and treatment assembly to provide a warning of an impending therapy to be delivered to the patient in response to a detected one or more arrhythmia conditions of the patient, receive from at least one of the first two user response buttons or the second at least one user response button a user input in response to the warning of the impending therapy, wherein the user input comprises at least one of the first two user response buttons being pressed simultaneously; or the second at least one user response button being pressed for a threshold duration and released; and wherein if the at least one of the first two user response buttons or the second at least one user response button is pressed for longer than the threshold duration without release, the processor is configured to prompt the patient to indicate consciousness by providing another user input via the housing of the arrhythmia monitoring and treatment assembly; and cause the arrhythmia monitoring and treatment assembly to suspend the impending therapy in response to the received user input from the at least one of the first two user response buttons or the second at least one user response button.

2. The system of claim 1, wherein the arrhythmia monitoring and treatment assembly comprises a first pad configured to be adhesively attached to the patient's torso, and a second pad configured to be adhesively attached to the patient's torso, wherein the housing is mounted on the first pad.

3. The system of claim 2, wherein
the first pad comprises a first at least one therapy electrode and a first at least one sensing electrode,
the second pad comprises a second at least one therapy electrode and a second at least one sensing electrode, and
the processor is configured to
receive the ECG signal sensed from the first and second at least one sensing electrodes, and
provide the therapy to the patient via the first and second at least one therapy electrodes.

4. The system of claim 1, wherein the first two user response buttons disposed on the housing of the arrhythmia monitoring and treatment assembly and the second at least one user response button are configured to be worn by the patient simultaneously.

5. The system of claim 4, further comprising a wearable article, wherein the wearable article comprises
the second at least one user response button, and
communications circuitry configured to transmit information relating to the user input from the second at least one user response button to the processor disposed in the arrhythmia monitoring and treatment assembly.

6. The system of claim 5, wherein the wearable article comprises at least one of a bracelet, a ring, a retractable pendant, a necklace, a belt configured to be worn over the clothing, a sash configured to be worn over the clothing, a bolo tie, a watch, an arm band, or a patch configured to be worn over the clothing of the patient at an accessible location.

7. The system of claim 5, wherein the wearable article is configured to be at least partially disposed under the clothing of the patient.

8. The system of claim 5, wherein the communications circuitry is configured to provide the information relating to the user input from the second at least one user response button via a wireless communications protocol.

9. The system of claim 8, wherein the second at least one user response button is uniquely paired with the arrhythmia monitoring and treatment assembly.

10. The system of claim 8 wherein the wireless communications protocol is at least one of Wi-Fi, BLUETOOTH, broadband cellular, and/or Long-Term Evolution (LTE), GSM/EDGE, or UMTS/HSPA.

11. The system of claim 5, further comprising a wired link extending between the arrhythmia monitoring and treatment assembly and the wearable article such that the communications circuitry and the processor are in wired communication.

12. The system of claim 11, wherein the wired link is configured to be detachable from one or both of the arrhythmia monitoring and treatment assembly and the wearable article.

13. The system of claim 11, wherein at least one of the arrhythmia monitoring and treatment assembly and the wearable article further comprises a retractable spool and pawl configured to adjust a length of the wired link.

14. The system of claim 5, wherein the wearable article further comprises one or more sensors configured to verify an identity of the patient based on at least one of audible, touch-based, signal-based, or visible information, and delay therapy delivery based at least in part on the verified identity.

15. The system of claim 5, wherein the second at least one user response button comprises at least one of a mechanically-actuatable button, a touch screen interface, or at least one touch screen button.

16. The system of claim 1, wherein the first two user response buttons are raised or depressed relative to a surface of the housing so as to be palpable beneath one or more layers of the clothing.

17. The system of claim 1, wherein the arrhythmia monitoring and treatment assembly further comprises
a plurality of ECG sensing electrodes and associated circuitry configured to monitor the ECG signal of the patient, and
a plurality of therapy electrodes and an associated therapy delivery circuit configured to deliver the therapy to the patient.

18. The system of claim 17, further comprising a garment configured to be worn about the torso of the patient to couple the arrhythmia monitoring and treatment device to the torso of the patient such that on delivering the therapy, one or more defibrillation or pacing pulses discharge into the torso via the plurality of therapy electrodes.

19. The system of claim 1, wherein the tallest height of the housing extends between around 1 to 10 cm from the skin surface of the patient.

20. The system of claim 1, wherein the tallest height of the housing extends between around 2 to 9 cm from the skin surface of the patient.

21. The system of claim 1, wherein the threshold duration comprises 5 seconds.

22. The system of claim 1, wherein the processor is further configured to prompt the patient to press the first two user response buttons disposed on the housing in response to the second at least one user response button being pressed for longer than the threshold duration and not released.

23. The system of claim 1, wherein the processor is configured to prompt the patient to indicate consciousness by tapping the housing of the arrhythmia monitoring and treatment assembly.

* * * * *

UNITED STATES PATENT AND TRADEMARK OFFICE
CERTIFICATE OF CORRECTION

| | |
|---|---|
| PATENT NO. | : 11,590,354 B2 |
| APPLICATION NO. | : 16/726283 |
| DATED | : February 28, 2023 |
| INVENTOR(S) | : Gary A. Freeman, Shane S. Volpe and James A. Patterson, III |

It is certified that error appears in the above-identified patent and that said Letters Patent is hereby corrected as shown below:

In the Specification

Column 28, Line 40 - delete "the a" and insert --the--

Column 33, Line 63 - delete "atria" and insert --atria.--

Column 37, Line 8 - delete "the an" and insert --an--

Column 41, Line 22 - delete "g" and insert --µF--

Signed and Sealed this
Fifteenth Day of August, 2023

Katherine Kelly Vidal
*Director of the United States Patent and Trademark Office*